(12) United States Patent
Czubryt

(10) Patent No.: US 9,238,685 B2
(45) Date of Patent: *Jan. 19, 2016

(54) INHIBITION OF COLLAGEN SYNTHESIS

(71) Applicant: University of Manitoba, Winnipeg (CA)

(72) Inventor: Michael P. Czubryt, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,879

(22) PCT Filed: Nov. 5, 2012

(86) PCT No.: PCT/CA2012/001018
§ 371 (c)(1),
(2) Date: May 2, 2014

(87) PCT Pub. No.: WO2013/063692
PCT Pub. Date: May 10, 2013

(65) Prior Publication Data
US 2014/0288003 A1 Sep. 25, 2014

Related U.S. Application Data

(60) Provisional application No. 61/555,735, filed on Nov. 4, 2011.

(51) Int. Cl.
| | | |
|---|---|---|
| *C07K 14/00* | (2006.01) | |
| *C07H 21/00* | (2006.01) | |
| *A61P 43/00* | (2006.01) | |
| *C07K 14/495* | (2006.01) | |
| *A61K 38/17* | (2006.01) | |
| *C07K 14/47* | (2006.01) | |

(52) U.S. Cl.
CPC ............... *C07K 14/495* (2013.01); *A61K 38/17* (2013.01); *C07K 14/4702* (2013.01)

(58) Field of Classification Search
CPC ... A61K 38/17; C07K 14/495; C07K 14/4702
See application file for complete search history.

(56) References Cited

U.S. PATENT DOCUMENTS

2007/0134650 A1  6/2007 Czubryt

FOREIGN PATENT DOCUMENTS

WO    2011/140639 A1    11/2011

OTHER PUBLICATIONS

Cserjesi et al, Scleraxis: a basic helix-loop-helix protein that prefigures skeletal formation during mouse embryogenesis, Development, 1995 121, pp. 1099-1110.*
Espira et al., "The basic helix-loop-helix transcription factor scelaxis regulates fibroblast collagen sythesis", Journal of Molecular and Cellular Cardiology, 47, pp. 188-195 (2009).
Bagchi et al., "Interaction of scleraxis and Smad-dependent cardiac collagen expression", The FASEB Journal, 25: 1032.5 (2011).
Czubryt et al., "Scleraxis: a novel target for anti-fibrotic therapy?", The FASEB Journal, 25: 1032.2 (2011).
International Preliminary Report on Patentability received in Application No. PCT/CA2012/001018, dated May 6, 2014.
Bagchi et al., "Synergistic roles of scleraxis and Smads in the regulation of collagen 1a2 gene expression", Biochmica et Biophysica Acta, 1823, pp. 1936-1944 (2012).

* cited by examiner

*Primary Examiner* — Julie Ha
*Assistant Examiner* — Li Ni Komatsu
(74) *Attorney, Agent, or Firm* — Alchemy-Partners, PC

(57) ABSTRACT

Therapies and compositions for reducing collagen synthesis in mammalian cells and tissues wherein the targets are scleraxis, sclerax-is-binding sites, receptor-regulated Smads, and/or binding sites for receptor-regulated Smads whereby synergistic interactions between scleraxis proteins and receptor-regulated Smads are reduced, inhibited, interfered with, stopped, and/or prevented thereby reducing, inhibiting and/or interfering with the activation of collagen 1α2 promoter thereby inhibiting collagen production in mammalian cells and tissues. Alternatively, the therapies and compositions may reduce, inhibit, interfere with, stop, and/or prevent binding of the collagen 1α2 promoter to DNA thereby inhibiting expression of the collagen 1α2 gene in mammalian cells and tissues.

6 Claims, 19 Drawing Sheets (A) Mouse Scleraxis Protein: SEQ ID NO:1

MSFAMLRSAPPPGRYLYPEVSPLSEDEDRGSESSGSDEKPCRVHAARCGLQGAR
RRAGGRRAAGSGPGPGGRPGREPRQRHTANARERDRTNSVNTAFTALRTLIPTEP
ADRKLSKIETLRLASSYISHLGNVLLVGEACGDGQPCHSGPAFFHSGRAGSPLPPP
PPPPPLARDGGENTQPKQICTFCLSNQRKLSKDRDRKTAIRS (B) Rat Scleraxis Protein: SEQ ID NO:2

MSFAMLRSAPPPGRYLYPEVSPLSEDEDRGSESSGSDEKPCRVHAARCGLQGAR
RRAGGRRAAGSGPGPGGRPGREPRQRHTANARERDRTNSVNTAFTALRTLIPTEP
ADRKLSKIETLRLASSYISHLGNVLLVGEACGDGQPCHSGPAFFHSGRAGSPLPPP
PPPPPLPLARDGGENTQPKQICTFCLSNQRKLSKDRDRKTAIRS (C) Human Scleraxis Protein: SEQ ID NO:3

MSFATLRPAPPGRYLYPEVSPLSEDEDRGSDSSGSDEKPCRVHAARCGLQGARR
RAGGRRAGGGGPGGRPGREPRQRHTANARERDRTNSVNTAFTALRTLIPTEPAD
RKLSKIETLRLASSYISHLGNVLLAGEACGDGQPCHSGPAFFHAARAGSPPPPPPP
PPARDGENTQPKQICTFCLSNQRKLSKDRDRKTAIRS (D)
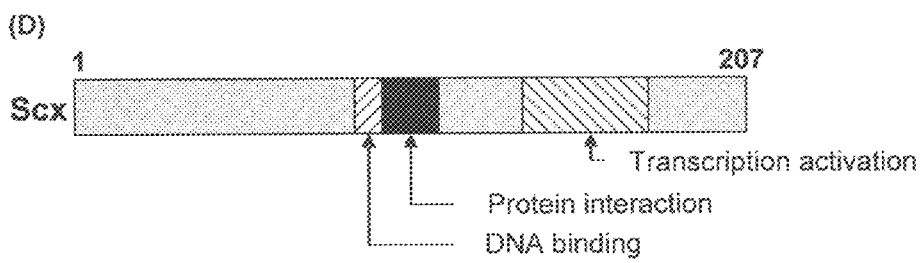
Transcription activation
Protein interaction
DNA binding (E)
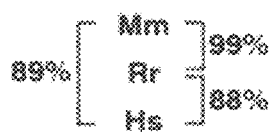

Fig. 1

(A) Mouse scleraxis (Scx) gene: SEQ ID NO:4

ATGTCCTTCGCCATGCTGCGTTCAGCGCCGCCGCCGGGTCGCTACCTGTACCC
TGAGGTGAGCCCGCTGTCGGAGGATGAGGACCGCGGAAGCGAGAGCTCGGG
CTCCGACGAGAAACCCTGCCGTGTGCATGCTGCGCGCTGTGGCCTCCAGGGC
GCCCGGCGGCGGGCAGGAGGACGGAGGGCCGCGGGTAGCGGGCCAGGACC
CGGGGGGCGGCCAGGCCGCGAGCCCCGGCAGCGGCACACAGCGAATGCGCG
CGAGCGGGACCGCACCAACAGCGTGAACACGGCCTTCACTGCGCTGCGCACA
CTCATCCCCACCGAGCCAGCGGACCGCAAGCTCTCCAAGATTGAGACGCTGCG
CCTGGCCTCCAGCTACATTTCTCACCTGGGCAATGTGCTGCTGGTGGGTGAGG
CCTGTGGCGACGGGCAACCATACATTTCTCACCTGGGCAATGTGCTGCTGGTG
GGTGAGGCCTGTGGCGACGGGCAACCATCGCCGCCACCACCACTGGCCAGAG
ACGGCGGCGAGAACACCCAGCCCAAACAGATCTGCACGCCGCCACCACCACT
GGCCAGAGACGGCGGCGAGAACACCCAGCCCAAACAGATCTGCAGAAGTTAG (B) Scx gene nucleotide sequence showing location of binding domain deletion:

ATGTCCTTCGCCATGCTGCGTTCAGCGCCGCCGCCGGGTCGCTACCTGTACCC
TGAGGTGAGCCCGCTGTCGGAGGATGAGGACCGCGGAAGCGAGAGCTCGGG
CTCCGACGAGAAACCCTGCCGTGTGCATGCTGCGCGCTGTGGCCTCCAGGGC
GCCCGGCGGCGGGCAGGAGGACGGAGGGCCGCGGGTAGCGGGCCAGGACC
CGGGGGGCGGCCAGGCCGCGAGCCC****************************************ACCAA
CAGCGTGAACACGGCCTTCACTGCGCTGCGCACACTCATCCCCACCGAGCCAG
CGGACCGCAAGCTCTCCAAGATTGAGACGCTGCGCCTGGCCTCCAGCTACATT
TCTCACCTGGGCAATGTGCTGCTGGTGGGTGAGGCCTGTGGCGACGGGCAAC
CATACATTTCTCACCTGGGCAATGTGCTGCTGGTGGGTGAGGCCTGTGGCGAC
GGGCAACCATCGCCGCCACCACCACTGGCCAGAGACGGCGGCGAGAACACCC
AGCCCAAACAGATCTGCACGCCGCCACCACCACTGGCCAGAGACGGCGGCGA
GAACACCCAGCCCAAACAGATCTGCAGAAGTTAG (C) ScxΔBD nucleotide sequence with the binding domain deleted: SEQ ID NO:5

ATGTCCTTCGCCATGCTGCGTTCAGCGCCGCCGCCGGGTCGCTACCTGTACCC
TGAGGTGAGCCCGCTGTCGGAGGATGAGGACCGCGGAAGCGAGAGCTCGGG
CTCCGACGAGAAACCCTGCCGTGTGCATGCTGCGCGCTGTGGCCTCCAGGGC
GCCCGGCGGCGGGCAGGAGGACGGAGGGCCGCGGGTAGCGGGCCAGGACC
CGGGGGGCGGCCAGGCCGCGAGCCCACCAACAGCGTGAACACGGCCTTCACT
GCGCTGCGCACACTCATCCCCACCGAGCCAGCGGACCGCAAGCTCTCCAAGAT
TGAGACGCTGCGCCTGGCCTCCAGCTACATTTCTCACCTGGGCAATGTGCTGC
TGGTGGGTGAGGCCTGTGGCGACGGGCAACCATACATTTCTCACCTGGGCAAT
GTGCTGCTGGTGGGTGAGGCCTGTGGCGACGGGCAACCATCGCCGCCACCAC
CACTGGCCAGAGACGGCGGCGAGAACACCCAGCCCAAACAGATCTGCACGCC
GCCACCACCACTGGCCAGAGACGGCGGCGAGAACACCCAGCCCAAACAGATC
TGCAGAAGTTAG

Fig. 2

(A) Scx nucleotide sequence with inserted FLAG and HA tags: SEQ ID NO:6

ATGGATTACAAGGACGACGACGATAAGATCTGTCGACGGTACCCCGGGGAATT
CTATCCGTATGATGTGCCGGATTATGCGATGTCCTTCGCCATGCTGCGTTCAGC
GCCGCCGCCGGGTCGCTACCTGTACCCTGAGGTGAGCCCGCTGTCGGAGGAT
GAGGACCGCGGAAGCGAGAGCTCGGGCTCCGACGAGAAACCCTGCCGTGTGC
ATGCTGCGCGCTGTGGCCTCCAGGGCGCCCGGCGGCGGGCAGGAGGACGGA
GGGCCGCGGGTAGCGGGCCAGGACCCGGGGGGCGGCCAGGCCGCGAGCCC
CGGCAGCGGCACACAGCGAATGCGCGCGAGCGGGACCGCACCAACAGCGTG
AACACGGCCTTCACTGCGCTGCGCACACTCATCCCCACCGAGCCAGCGGACC
GCAAGCTCTCCAAGATTGAGACGCTGCGCCTGGCCTCCAGCTACATTTCTCAC
CTGGGCAATGTGCTGCTGGTGGGTGAGGCCTGTGGCGACGGGCAACCATACA
TTTCTCACCTGGGCAATGTGCTGCTGGTGGGTGAGGCCTGTGGCGACGGGCAA
CCATCGCCGCCACCACCACTGGCCAGAGACGGCGGCGAGAACACCCAGCCCA
AACAGATCTGCACGCCGCCACCACCACTGGCCAGAGACGGCGGCGAGAACAC
CCAGCCCAAACAGATCTGCAGAAGTTAG (B) ScxΔBD nucleotide sequence with inserted FLAG and HA tags: SEQ ID NO:7

ATGGATTACAAGGACGACGACGATAAGATCTGTCGACGGTACCCCGGGGAATT
CTATCCGTATGATGTGCCGGATTATGCGATGTCCTTCGCCATGCTGCGTTCAGC
GCCGCCGCCGGGTCGCTACCTGTACCCTGAGGTGAGCCCGCTGTCGGAGGAT
GAGGACCGCGGAAGCGAGAGCTCGGGCTCCGACGAGAAACCCTGCCGTGTGC
ATGCTGCGCGCTGTGGCCTCCAGGGCGCCCGGCGGCGGGCAGGAGGACGGA
GGGCCGCGGGTAGCGGGCCAGGACCCGGGGGGCGGCCAGGCCGCGAGCCC
ACCAACAGCGTGAACACGGCCTTCACTGCGCTGCGCACACTCATCCCCACCGA
GCCAGCGGACCGCAAGCTCTCCAAGATTGAGACGCTGCGCCTGGCCTCCAGC
TACATTTCTCACCTGGGCAATGTGCTGCTGGTGGGTGAGGCCTGTGGCGACGG
GCAACCATACATTTCTCACCTGGGCAATGTGCTGCTGGTGGGTGAGGCCTGTG
GCGACGGGCAACCATCGCCGCCACCACCACTGGCCAGAGACGGCGGCGAGAA
CACCCAGCCCAAACAGATCTGCACGCCGCCACCACCACTGGCCAGAGACGGC
GGCGAGAACACCCAGCCCAAACAGATCTGCAGAAGTTAG (C) Protein expressed by the ScxΔBD mutant: SEQ ID NO:8

MSFAMLRSAPPPGRYLYPEVSPLSEDEDRGSESSGSDEKPCRVHAARCGLQGARRRA
GGRRAAGSGPGPGGRPGREPTNSVNTAFTALRTLIPTEPADRKLSKIETLRLASSYISHL
GNVLLVGEACGDGQPCHSGPAFFHSGRAGSPLPPPPPPPLARDGGENTQPKQICTFC
LSNQRKLSKDRDRKTAIRS

Fig. 3

INHIBITION OF COLLAGEN SYNTHESIS

This application is a national phase application under 35 U.S.C. § of International Patent Application No. PCT/CA2012/001018 filed on Nov. 5, 2012 which claims the benefit of U.S. Provisional Application Serial No. 61/555,735 filed on Nov. 4, 2011, the entire text of each of the above-referenced disclosures is specifically incorporated herein by reference without disclaimer.

TECHNICAL FIELD

Various embodiments generally relate to compositions, therapies, and methods of use of the compositions and/or therapies for inhibiting production of collagen in mammalian tissues. More particularly, the present invention relates to compositions, therapies, and methods for inhibiting activation of the collagen 1α2 promoter thereby inhibiting expression of the collagen 1α2 gene in mammalian cells.

BACKGROUND ART

Fibrosis is a general term used to describe excessive formation and/or development of fibrous connective tissues in mammalian tissues and organs as a consequence of an injury reparative process or a reaction to an abnormal causative agent. Prolonged fibrosis typically results in localized scarring of tissues and/or organs to the point where their physiological functions are impaired. Mammalian tissues and organs commonly affected by fibrosis include skin (e.g., sclerodermic fibrosis; keloid fibrosis), the heart (cardiac fibrosis; endomyocardial fibrosis), lungs (pulmonary fibrosis), liver (cirrhosis), and kidneys (nephrogenic fibrosis) among others. Fibrosis is associated with the over-production of collagen proteins which are the primary protein constituents of connective tissues.

Recent published information indicates that development of cardiac fibrosis resulting from tissue damage that occurs during myocardial infarctions is a consequence of a significant increase in scleraxis proteins in the damaged cardiac tissue areas. The increased scleraxis levels appear to be directly related to the activation of cardiac fibroblasts that are subsequently phenoconverted to myofibroblasts as part of the wound healing response. Concomitant changes occurring in the damaged cardiac tissue include degradation of necrotic myocytes, repopulation of the damaged infarct area by myofibroblasts, and subsequent remodeling of the surrounding extracellular matrix (ECM) to form scar tissues. Although the mechanisms controlling the phenoconversion of cardiac fibroblasts to myofibroblasts are not yet well understood, it appears that this differentiation process is strongly promoted by the fibrotic agent TGF-$\beta_1$ which in turn, appears to cause increased scleraxis protein levels in the damaged areas. Collagen production is regulated in part by the COL1α2 gene. The proximal COL1α2 gene promoter is responsive to TGF-$\beta_1$ signaling and to scleraxis. Accordingly, increasing levels of scleraxis proteins directly or in response to TGF-β1 signaling in infarct-affected tissues will promote COL1α2 gene expression and production of collagen.

The activation of the cardiac fibroblasts and their phenoconversion to myofibroblasts significantly increases expression and proliferation of types I, III and V fibrillar collagens in the infarct-damaged areas. However, post-infarct development and proliferation of cardiac scar tissue often extends beyond damaged areas to the point where the cardiac contractility is impaired, and thereby may contribute to heart failure.

There is need, therefore, for compositions and therapies that will enable selective inhibition of the expression of COL1α2 genes in damaged tissues.

SUMMARY OF THE INVENTION

This section provides a general summary of the disclosure and is not a comprehensive disclosure of its full scope.

Methods are disclosed for reducing, inhibiting, interfering with, stopping, preventing expression of and/or production of and/or accumulation of collagen in mammalian cells by reducing, inhibiting, interfering with, stopping, and/or preventing synergistic interactions between scleraxis proteins and/or receptor-regulated Smads whereby the activation of collagen 1α2 promoter is reduced, inhibited, interfered with, thereby inhibiting collagen production in mammalian cells and tissues. Some methods may reduce, inhibit, interfere with, stop, and/or prevent the expression and/or production of scleraxis proteins, or alternatively, with the ability of scleraxis proteins to synergistically interact with receptor-regulated Smads. Some methods may reduce, inhibit, interfere with, stop, and/or prevent the expression and/or production of receptor-regulated Smads, or alternatively, with the ability of receptor-regulated Smads to synergistically interact with scleraxis proteins. Some methods may reduce, inhibit, interfere with, stop, prevent expression of and/or production of and/or accumulation of collagen in mammalian cells by providing to mammalian cells a basic domain deletion mutant derived from scleraxis cDNA and named ScxΔBD to bind with receptor-regulated Smads thereby: (i) reducing, inhibiting, interfering with, stopping, and/or preventing synergistic interactions between scleraxis proteins and/or receptor-regulated Smads, and/or alternatively (ii) reducing, inhibiting, interfering with, stopping, and/or preventing receptor-regulated Smads binding to DNA, thereby inhibiting activation of the collagen 1α2 promoter.

Also disclosed are therapies for reducing, inhibiting, interfering with, stopping, preventing expression of and/or production of and/or accumulation of collagen in mammalian cells by reducing, inhibiting, interfering with, stopping, and/or preventing synergistic interactions between scleraxis proteins and/or receptor-regulated Smads whereby the activation of collagen 1α2 promoter is reduced, inhibited, interfered with, thereby inhibiting collagen production in mammalian cells and tissues. Some therapies may reduce, inhibit, interfere with, stop, and/or prevent the expression and/or production of scleraxis proteins, or alternatively, with the ability of scleraxis proteins to synergistically interact with receptor-regulated Smads. Some therapies may reduce, inhibit, interfere with, stop, and/or prevent the expression and/or production of receptor-regulated Smads, or alternatively, with the ability of receptor-regulated Smads to synergistically interact with scleraxis proteins. Some therapies may reduce, inhibit, interfere with, stop, prevent expression of and/or production of and/or accumulation of collagen in mammalian cells by providing to mammalian cells a basic domain deletion mutant derived from scleraxis cDNA and named ScxΔBD to bind with receptor-regulated Smads thereby: (i) reducing, inhibiting, interfering with, stopping, and/or preventing synergistic interactions between scleraxis proteins and/or receptor-regulated Smads, and/or alternatively (ii) reducing, inhibiting, interfering with, stopping, and/or preventing receptor-regulated Smads binding to DNA, thereby inhibiting activation of the collagen 1α2 promoter. Exemplary therapies include but are not limited to administration of compositions that: (i) have scleraxis production and/or receptor-regulated Smads as targets, (ii) compete with scleraxis activators and/or receptor-regulated Smads for binding sites. Other exemplary therapies include administration of compositions that aggressively bind to unbound receptor-regulated Smads and/or scleraxis proteins. Other exemplary therapies include providing expression of or alternatively delivery of the basic domain deletion mutant ScxΔBD into mammalian cells thereby to bind with receptor-regulated Smads thereby: (i) reducing, inhibiting, interfering with, stopping, and/or preventing synergistic interactions between scleraxis proteins and/or receptor-regulated Smads, and/or alternatively (ii) reducing, inhibiting, interfering with, stopping, and/or preventing receptor-regulated Smads binding to DNA, thereby inhibiting activation of the collagen 1α2 promoter.

This disclosure also pertains to use of compositions for reducing, inhibiting, interfering with, stopping, preventing expression, production, accumulation of scleraxis and/or receptor-regulated Smads in mammalian cells, thereby reducing, inhibiting, interfering with, stopping, preventing activation of collagen 1α2 promoter, which in turn, results in reducing, inhibiting, interfering with, stopping, preventing collagen production in mammalian cells. Some compositions may be used to deliver the basic domain deletion mutant ScxΔBD into mammalian cells and/or facilitate and/or enhance the expression of the basic domain deletion mutant ScxΔBD so that it may bind with receptor-regulated Smads thereby reducing, inhibiting, interfering with, stopping, preventing activation of collagen 1α2 promoter by receptor-regulated Smads. Suitable receptor-regulated Smad targets for the compositions are Smad1, Smad2, Smad3, Smad5, Smad8/9.

Further areas of applicability will become apparent from the disclosure provided herein. The description and specific examples in this summary are intended for the purposes of illustration only and are not intended to limit the scope of the present disclosure.

BRIEF DESCRIPTION OF THE DRAWINGS

The drawings described herein are for illustrative purposes only of selected embodiments and are not intended to limit the scope of the present disclosure.

FIG. 1(A) shows the amino acid sequence listing (SEQ ID NO:1) for a normal mouse scleraxis protein, FIG. 1(B) shows the amino acid sequence listing (SEQ ID NO:2) for a normal rat scleraxis protein, FIG. 1(C) shows the amino acid sequence listing (SEQ ID NO:3) for a normal human scleraxis protein, FIG. 1(D) shows a map of the scleraxis protein, and FIG. 1(E) shows the homologies between the mouse scleraxis protein, the rat scleraxis protein, and the human scleraxis protein;

FIG. 2(A) shows the nucleotide sequence listing (SEQ ID NO:4) of the mouse Scx cDNA, FIG. 2(B) shows the location of the binding domain deletion from the mouse Scx nucleotide sequence listing, and FIG. 2(C) shows the nucleotide sequence listing (SEQ ID NO:5) for the scleraxis basic domain deletion ScxΔABD mutant;

FIG. 3(A) shows the mouse Scx sequence listing into which the FLAG and HA tags have been inserted (SEQ ID NO:6), FIG. 3(B) shows the ScxΔABD nucleotide sequence listing into which the FLAG and HA tags have been inserted, and FIG. 3(C) shows the amino acid sequence listing (SEQ ID NO:8) for the protein expressed by the basic domain deletion ScxΔABD mutant;

DETAILED DESCRIPTION OF THE INVENTION

Figure 4:
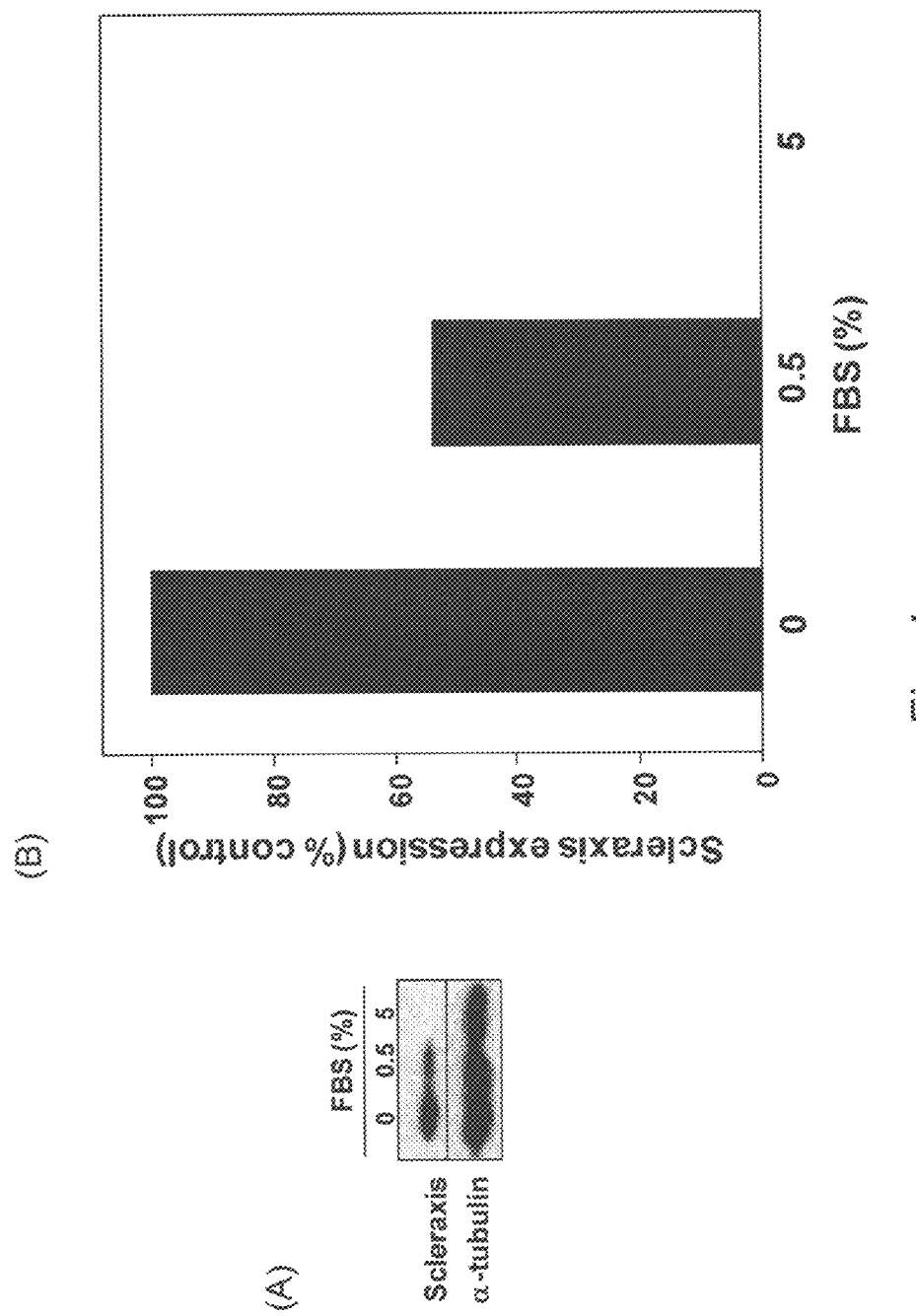
FIG. 4(A) is a micrograph showing detection of α-tubulin and scleraxis expression in rabbit aorta smooth muscle cells in the absence and presence of serum deprivation.
FIG. 4(B) is a chart showing the effect of serum deprivation on scleraxis expression in rabbit aorta smooth muscle cells.

The present disclosure relates to novel nucleotide sequences, novel proteins, compositions comprising the novel nucleotide sequences, compositions comprising the novel proteins, use of the compositions as antagonists of scleraxis protein expression and/or scleraxis accumulation and/or scleraxis activity in damaged mammalian tissues or organs for reducing, inhibiting, interfering with production of collagen. The present disclosure also relates to therapies, and kits comprising novel nucleotide sequences, novel proteins, compositions comprising the novel nucleotide sequences. In particular, the embodiments of the present invention relate to a novel basic domain deletion mutant named "ScxΔBD". The basic domain deletion ScxΔBD mutant is derived from scleraxis cDNA.

The present disclosure also relates to the delivery of and/or expression of the basic domain deletion ScxΔBD mutant in mammalian cells wherein they bind with receptor-regulated Smads thereby: (i) reducing, inhibiting, interfering with, stopping, and/or preventing synergistic interactions between receptor-regulated Smads and scleraxis, and/or alternatively (ii) reducing, inhibiting, interfering with, stopping, and/or preventing receptor-regulated Smads binding to DNA, thereby inhibiting activation of the collagen 1α2 promoter. In other words, the basic domain deletion ScxΔBD mutant can be usd to substitute and/or compete with scleraxis proteins for binding with Smads thereby reducing, inhibiting, interfering with, stopping, and/or preventing receptor-regulated Smads binding to DNA.

The present disclosure also relates to methods for reducing, inhibiting, interfering with, stopping, preventing expression of and/or production of and/or accumulation of collagen in mammalian cells by reducing, inhibiting, interfering with, stopping, preventing expression, production, accumulation of scleraxis and/or receptor-regulated Smads whereby the activation of collagen 1α2 promoter is reduced, inhibited, interfered with.

The present disclosure also relates to therapies for reducing, inhibiting, interfering with, stopping, preventing expression of and/or production of and/or accumulation of collagen in mammalian cells by reducing, inhibiting, interfering with, stopping, preventing expression, production, accumulation of scleraxis and/or receptor-regulated Smads whereby the activation of collagen 1α2 promoter is reduced, inhibited, interfered with.

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "scleraxis" as used herein refers to a protein that is a transcription factor with a basic helix-loop-helix (bHLH) motif and includes any form of scleraxis from any species as well as analogs and homologs thereof. Scleraxis proteins are exemplified herein by amino acid sequence listings SEQ ID NO:1, SEQ ID NO:2, and SEQ ID NO:3.

The term "Smads" as used herein refers to receptor-regulated intracellular proteins that are activated by extracellular signals such as those exemplified by transforming growth factor (TGF) β ligands. For example, receptor-regulated Smads transduce TGF-β ligands to cell nuclei where they activate downstream TGF-β-mediated gene transcription. Receptor-regulated Smads include Smad1, Smad2, Smad3, Smad5, and Smad8/9. Antagonist/inhibitory Smads include Smad6 and Smad7. Smad4 is a common-mediator Smad.

The term "abrogate" as used herein means to suppress and/or interfere with and/or prevent and/or eliminate.

The term "modulate scleraxis" as used herein means to inhibit and/or suppress the expression and/or formation and/or development and/or functional activity of scleraxis proteins.

The term "modulate collagen synthesis" as used herein means to inhibit and/or suppress the formation and/or development of collagen.

The term "effective amount" as used herein means an amount effective, at dosages and for periods of time necessary to achieve the desired results (e.g. the modulation of collagen synthesis). Effective amounts of a molecule may vary according to factors such as the disease state, age, sex, weight of the animal. Dosage regimes may be adjusted to provide the optimum therapeutic response. For example, several divided doses may be administered daily or the dose may be proportionally reduced as indicated by the exigencies of the therapeutic situation.

The term "subject" as used herein includes all members of the animal kingdom, and specifically includes humans.

The term "a cell" includes a single cell as well as a plurality or population of cells. Administering an agent to a cell includes both in vitro and in vivo administrations.

The term "about" or "approximately" means within 20%, preferably within 10%, and more preferably within 5% of a given value or range.

The term "nucleic acid" refers to a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semisynthetic DNA.

The term "gene" refers to an assembly of nucleotides that encode a polypeptide, and includes cDNA and genomic DNA nucleic acids.

The term "recombinant DNA molecule" refers to a DNA molecule that has undergone a molecular biological manipulation.

The term "vector" refers to any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

The term "cloning vector" refers to a replicon, such as plasmid, phage or cosmid, to which another DNA segment may be attached so as to bring about the replication of the attached segment. Cloning vectors may be capable of replication in one cell type, and expression in another ("shuttle vector").

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

The term "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

Modification of a genetic and/or chemical nature is understood to mean any mutation, substitution, deletion, addition and/or modification of one or more residues. Such derivatives may be generated for various purposes, such as in particular that of enhancing its production levels, that of increasing and/or modifying its activity, or that of conferring new pharmacokinetic and/or biological properties on it. Among the derivatives resulting from an addition, there may be mentioned, for example, the chimeric nucleic acid sequences comprising an additional heterologous part linked to one end, for example of the hybrid construct type consisting of a cDNA with which one or more introns would be associated.

Likewise, for the purposes of the invention, the claimed nucleic acids may comprise promoter, activating or regulatory sequences, and the like.

The term "promoter sequence" refers to a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

The term "homologous" in all its grammatical forms and spelling variations refers to the relationship between proteins that possess a "common evolutionary origin," including homologous proteins from different species. Such proteins (and their encoding genes) have sequence homology, as reflected by their high degree of sequence similarity. This homology is greater than about 75%, greater than about 80%, greater than about 85%. In some cases the homology will be greater than about 90% to 95% or 98%.

"Amino acid sequence homology" is understood to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence.

The term "polypeptide" refers to a polymeric compound comprised of covalently linked amino acid residues. Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

The term "protein" refers to a polypeptide which plays a structural or functional role in a living cell.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "derivative" refers to a product comprising, for example, modifications at the level of the primary structure, such as deletions of one or more residues, substitutions of one or more residues, and/or modifications at the level of one or more residues. The number of residues affected by the modifications may be, for example, from 1, 2 or 3 to 10, 20, or 30 residues. The term derivative also comprises the molecules comprising additional internal or terminal parts, of a peptide nature or otherwise. They may be in particular active parts, markers, amino acids, such as methionine at position ~1. The term derivative also comprises the molecules comprising modifications at the level of the tertiary structure (N-terminal end, and the like). The term derivative also comprises sequences homologous to the sequence considered, derived from other cellular sources. and in particular from cells of human origin, or from other organisms, and possessing activity of the same type or of substantially similar type. Such homologous sequences may be obtained by hybridization experiments. The hybridizations may be performed based on nucleic acid libraries, using, as probe, the native sequence or a fragment thereof, under conventional stringency conditions or preferably under high stringency conditions.

Scleraxis proteins expressed by mouse Scx cDNA (FIG. 1(A)) are exemplified by nucleotide sequence SEQ ID NO:1, by rat Scx cDNA (FIG. 1(B)) are exemplified by SEQ ID NO:2, and by human Scx cDNA (FIG. 1(C)) are exemplified by SEQ ID NO:3, and show a high degree of homology. Human scleraxis protein shows an 89% homology with mouse scleraxis protein (FIG. 1(E)) and an 88% homology with rat scleraxis protein (FIG. 1(E)). FIG. 1(D) shows the functional regions of the scleraxis proteins.

I have surprisingly discovered that deleting a basic DNA binding domain region (indicated by "*" in FIG. 2(B)) from mouse Scx nucleotide sequence SEQ ID NO:4 (FIG. 2(A)) provides a nucleotide sequence SEQ ID NO:5 that comprises a basic domain deletion mutant named herein as the ScxΔBD mutant (FIG. 2(C)). The basic domain deletion ScxΔBD mutant expresses a novel protein having a nucleotide sequence shown in FIG. 2(C) and named SEQ ID NO:8. I further surprisingly discovered that the ScxΔBD protein is an antagonist of scleraxis and significantly reduces activation of and/or expression of Scx genes and of COL1α2 genes.

Accordingly, an embodiment of the present invention pertains to novel basic domain deletion ScxΔBD mutants exemplified by SEQ ID NO:5, and includes nucleotide sequences having about 75% or greater homology with SEQ ID NO:5, about 80% or greater homology with SEQ ID NO:5, about 85% or greater homology with SEQ ID NO:5, about 90% or greater homology with SEQ ID NO:5, about 95% or greater homology with SEQ ID NO:5. An aspect pertains to use of the basic domain deletion ScxΔBD mutants exemplified by SEQ ID NO:5, to abrogate expression of and/or the functional activity of scleraxis proteins and/or to modulate collagen synthesis. Other aspects pertain to the use of basic domain deletion ScxΔBD mutants for production of novel proteins comprising amino acid sequences exemplified by SEQ ID NO:8.

Another embodiment of the present invention pertains to novel proteins expressed by basic domain deletion ScxΔBD mutants comprising nucleotide sequence SEQ ID NO:5 wherein the novel proteins comprise amino acid sequences exemplified by SEQ ID NO:8, and includes amino acid sequences having about 75% or greater homology with SEQ ID NO:8, about 80% or greater homology with SEQ ID NO:8, about 85% or greater homology with SEQ ID NO:8, about 90% or greater homology with SEQ ID NO:8, about 95% or greater homology with SEQ ID NO:8.

Another embodiment of the present invention pertains to compositions comprising novel proteins expressed by basic domain deletion ScxΔBD mutants exemplified by SEQ ID NO:5 wherein the novel proteins comprise amino acid sequences exemplified by SEQ ID NO:8, and includes amino acid sequences having about 75% or greater homology with SEQ ID NO:8, about 80% or greater homology with SEQ ID NO:8, about 85% or greater homology with SEQ ID NO:8, about 90% or greater homology with SEQ ID NO:8, about 95% or greater homology with SEQ ID NO:8. The compositions are useful for abrogating expression and/or the functional activity of scleraxis proteins and/or to modulate collagen synthesis.

Those skilled in these arts will understand that microbial cells exemplified by bacterial cells and yeast cells can be transformed by incorporation therein of SEQ ID NO:5 or a derivative thereof using commercially available vectors and well-known methodologies. Suitable bacterial cells are exemplified by *Escherichia colil, Pseudomonas* spp., and *Bacillus* spp. Suitable yeast cells are exemplified by *Zygosaccharomyces* spp., *Saccharomyces* spp., *Pichia* spp., or *Kluveromyces* spp. The transformed microbial cells can then be cultured to express proteins comprising amino acid sequences exemplified by SEQ ID NO:8. The proteins can be recovered and used as constituents in pharmaceutical compositions.

The present invention includes pharmaceutical compositions containing one or more novel proteins expressed by basic domain deletion ScxΔBD mutants exemplified by SEQ ID NO:5 wherein the novel proteins comprise amino acid sequences exemplified by SEQ ID NO:8, and includes amino acid sequences having about 75% or greater homology with SEQ ID NO:8, about 80% or greater homology with SEQ ID NO:8, about 85% or greater homology with SEQ ID NO:8, about 90% or greater homology with SEQ ID NO:8, about 95% or greater homology with SEQ ID NO:8. Accordingly, the present invention provides a pharmaceutical composition comprising an effective amount of a novel protein expressed by basic domain deletion ScxΔBD mutants in admixture with a suitable diluent or carrier.

In one embodiment, the present invention provides a pharmaceutical composition for use in inhibiting collagen synthesis comprising an effective amount of a novel protein expressed by basic domain deletion ScxΔBD mutants in admixture with a suitable diluent or carrier.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The novel protein expressed by basic domain deletion ScxΔBD mutants can be injected intravenously, intraperitoneally or subcutaneously.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other modulatory agents.

Another embodiment of the present invention pertains to therapies for modulating fibrosis in a subject comprising using a viral vector or a non-viral vector for delivery to the subject of a nucleotide sequence comprising SEQ ID NO:5, and includes nucleotide sequences having about 75% or greater homology with SEQ ID NO:5, about 80% or greater homology with SEQ ID NO:5, about 85% or greater homology with SEQ ID NO:5, about 90% or greater homology with SEQ ID NO:5, about 95% or greater homology with SEQ ID NO:5.

The novel nucleotide sequences, novel proteins, and novel compositions of the present invention are useful for modulating scleraxis and/or collagen synthesis in a subject in need thereof to modulate and/or prevent fibrosis conditions exemplified by cardiac fibrosis; endomyocardial fibrosis, sclerodermic fibrosis, keloid fibrosis, pulmonary fibrosis, cirrhosis, nephrogenic fibrosis, and the like.

In addition, we also have surprisingly discovered that scleraxis proteins functionally interact with Smads in a synergistic manner to regulate the human collagen 1α2 proximal promoter. For example, increasing levels of scleraxis proteins and Smad3, a receptor-regulated Smad, above base levels in fibroblast cells results in a significant increase in synergistic activation of the collagen 1α2 proximal promoter. However, increasing the levels of scleraxis and Smad7, an antagonistic/inhibitory Smad, above base levels in fibroblast cells does not result in a scleraxis-stimulated effect on the production of the collagen 1α2 proximal promoter. In fact, combining Smad7 with scleraxis blocked the ability of scleraxis to stimulate the collagen 1α2 promoter. It is apparent that scleraxis and Smad3 synergistically promote activation of the collagen 1α2 promoter. Furthermore, interfering with the expression of scleraxis and/or expression of receptor-regulated Smads such as Smad1, Smad2, Smad3, Smad5, and Smad8/9, will result in reduced activation of the collagen 1α2 promoter resulting in reduced expression of the COL1α2 gene and the subsequent production of collagen.

Accordingly, this disclosure also pertains to therapies for reducing, inhibiting, interfering with, stopping, preventing collagen production in mammalian cells by reducing, inhibiting, interfering with, stopping, preventing expression, production, accumulation of scleraxis and/or a receptor-regulated Smad in mammalian cells, thereby reducing, inhibiting, interfering with, stopping, preventing activation of collagen 1α2 promoter. Such therapies can include but are not limited to administration of compositions that: (i) have scleraxis production and/or receptor-regulated Smads as targets, (ii) compete with scleraxis activators and/or receptor-regulated Smads for binding sites. Other suitable therapies include administration of compositions that aggressively bind to unbound receptor-regulated Smads and/or scleraxis proteins.

This disclosure also pertains to use of compositions for reducing, inhibiting, interfering with, stopping, preventing expression, production, accumulation of scleraxis and/or a receptor-regulated Smad in mammalian cells, thereby reducing, inhibiting, interfering with, stopping, preventing activation of collagen 1α2 promoter, which in turn, results in reducing, inhibiting, interfering with, stopping, preventing collagen production in mammalian cells. A suitable receptor-regulated Smad target for the compositions is Smad1, Smad2, Smad3, Smad5, Smad8/9.

The following examples are provided to more fully describe the invention and are presented for non-limiting illustrative purposes.

EXAMPLES

Example 1

I have surprisingly found that increasingly stressing aortic vascular smooth muscle cells by serum deprivation resulted in increasing expression of scleraxis (FIG. 4). Samples of rabbit aortic vascular smooth muscle cells were subjected to serum deprivation (0% FBS) to induce collagen synthesis, or were treated with low concentrations (0.5% FBS) or high concentrations (5% FBS) for 72 hours. Total protein was isolated from each sample for immunoblotting. α-tubulin was used as the loading control (FIG. 4(A)). Cells maintained in 5% serum did not express detectable amounts of scleraxis (FIG. 4(B)). However, increasing levels of serum deprivation resulted in increasing levels of scleraxis expression (FIG. 4(B)).

I also surprisingly found that pro-fibrotic TGF-β factor induces scleraxis expression in human airway smooth muscle cells. Samples of human airway smooth muscle cells were treated with 2.5 ng/mL TGF-$β_1$ for one of 30 min, 60 min, or 120 min. Total protein was isolated from each sample for immunoblotting. α-tubulin was used as the loading control (FIG. 5(A)). The data in FIG. 5(B) demonstrate that scleraxis was up-regulated in a time-dependent manner in response to treatment with TGF-$β_1$ (FIG. 5((B)).

Figure 5:
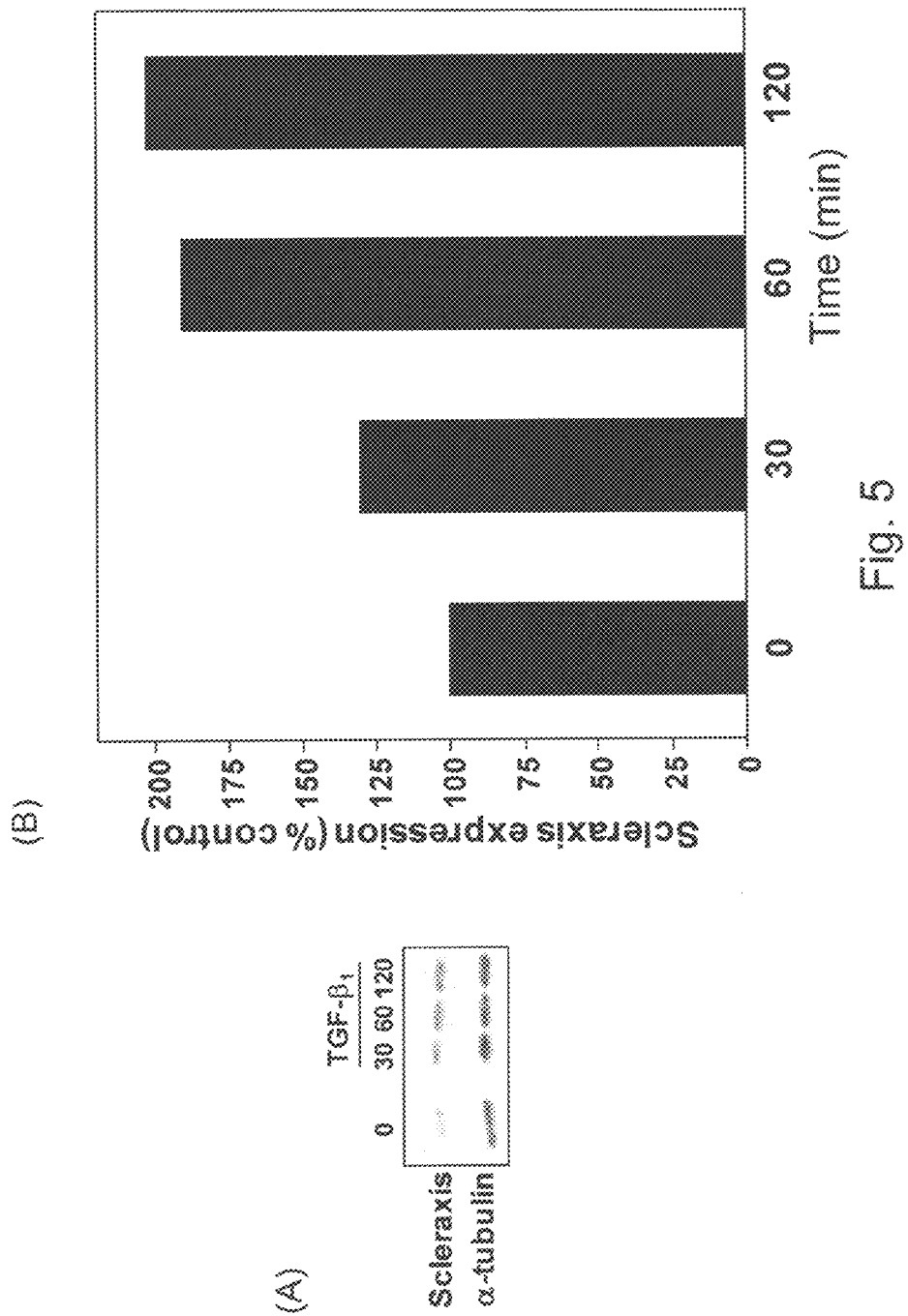
FIG. 5(A) is a micrograph showing the effects of pro-fibrotic TGF-β on detection of α-tubulin and scleraxis expression in human airway smooth muscle cells.
FIG. 5(B) is a chart showing the effect of pro-fibrotic TGF-β on scleraxis expression in human airway smooth muscle cells.

The data shown in FIGS. 4 and 5 demonstrate that induction of collagen synthesis in quiescent non-cardiac tissue is directly associated with increased levels of scleraxis. Therefore, according to one embodiment of the present invention, modulation of scleraxis expression and accumulation in mammalian systems will directly affect COL1α2-mediated production of collagen, and consequently directly affect development of fibrosis in non-cardiac tissues as well as in cardiac tissues.

Example 2

Figure 6:
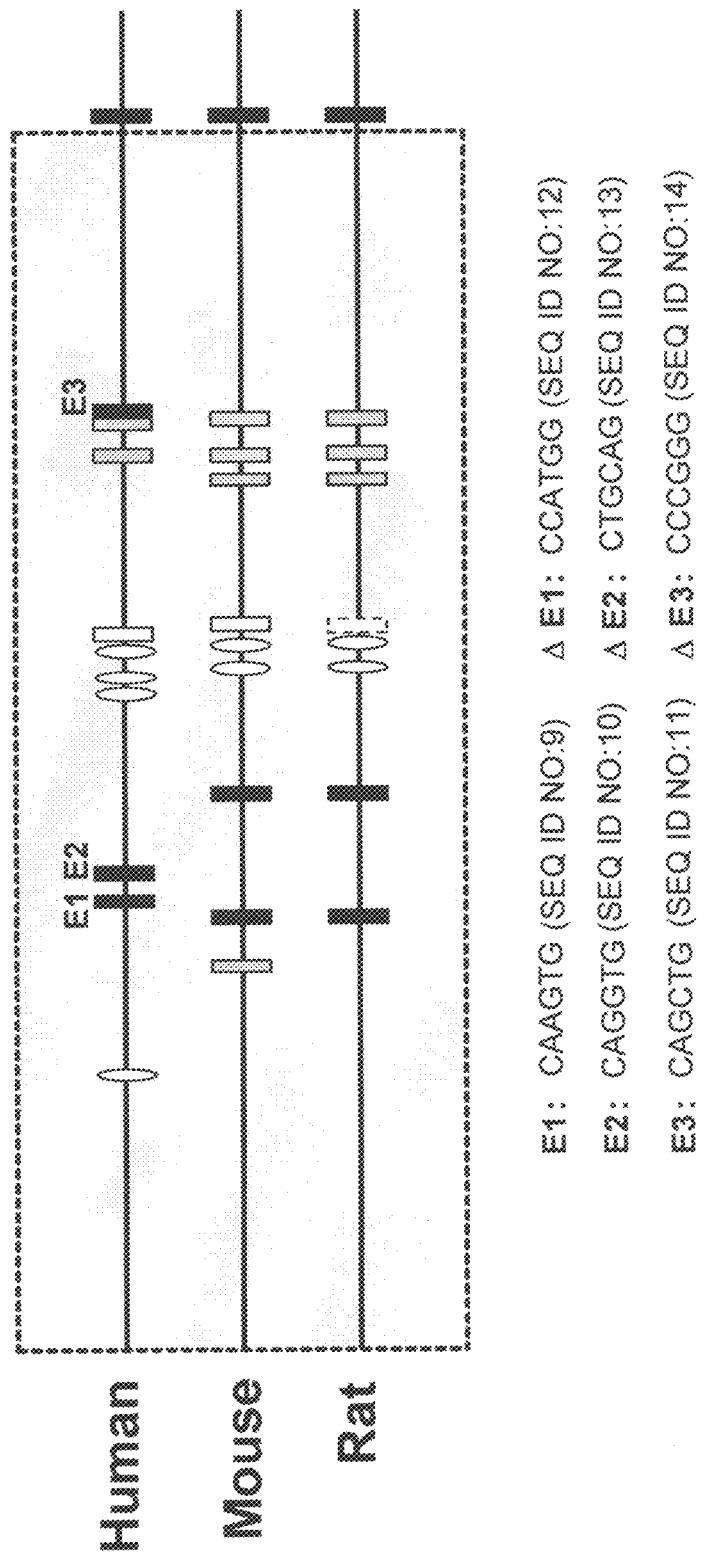
FIG. 6 shows a schematic representation of proximal human collagen 1α2 promoter, proximal mouse collagen 1α2 promoter, and proximal rat collagen 1α2 promoter.

The proximal COL1α2 gene promoter is rich in binding sites for transcription factors that regulate collagen synthesis. Such transcription factors include Sp1, Sp3, and Smads. Therefore, a study was done to identify potential scleraxis binding sites in this promoter. Three suitable putative E boxes were identified (FIG. 6). The proximal COL1α2 gene promoter (grey outline, FIG. 6) spans a region from −652 to +54 relative to the transcription start site and contains putative E boxes denoted E1 (SEQ ID NO:9), E2 (SEQ ID NO:10), and E3 (SEQ ID NO: 11) (black boxes, FIG. 6) that match the consensus "CANNTG" E box sequence. This region also contains binding sites for other transcription factors known to affect COL1α2 gene expression. These include SP 1 GC boxes (white ovals, FIG. 6), Sp1/SP3 T boxes (grey rectangles, FIG. 6), and a SMAD binding element (white rectangle, FIG. 6). The E box mutations used in this study are also shown in FIG. 6 (ΔE1, SEQ ID NO:12; ΔE2, SEQ ID NO:13; ΔE3, SEQ ID NO:14).

Figure 7:
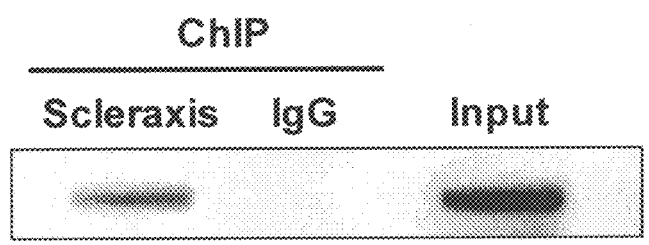
FIG. 7 is a micrograph showing binding of scleraxis to the rat COL1α2 proximal promoter.

The ability of scleraxis to bind to the proximal COL1α2 gene promoter in vivo was confirmed using adult rat P0 cardiac fibroblasts. Proteins produced in the samples and bound to the COL1α2 promoter were then immunoprecipitated using anti-scleraxis antibodies or non-specific antibodies (IgG negative control). The positive control consisted of the input genomic DNA. The primers used amplified a region from the rat COL1α2 proximal promoter that corresponded to E boxes 1 and 2 shown in FIG. 6. FIG. 7 shows that the adult rat P0 cardiac fibroblasts bound scleraxis on the COL1α2 promoter.

Example 3

Figure 8:
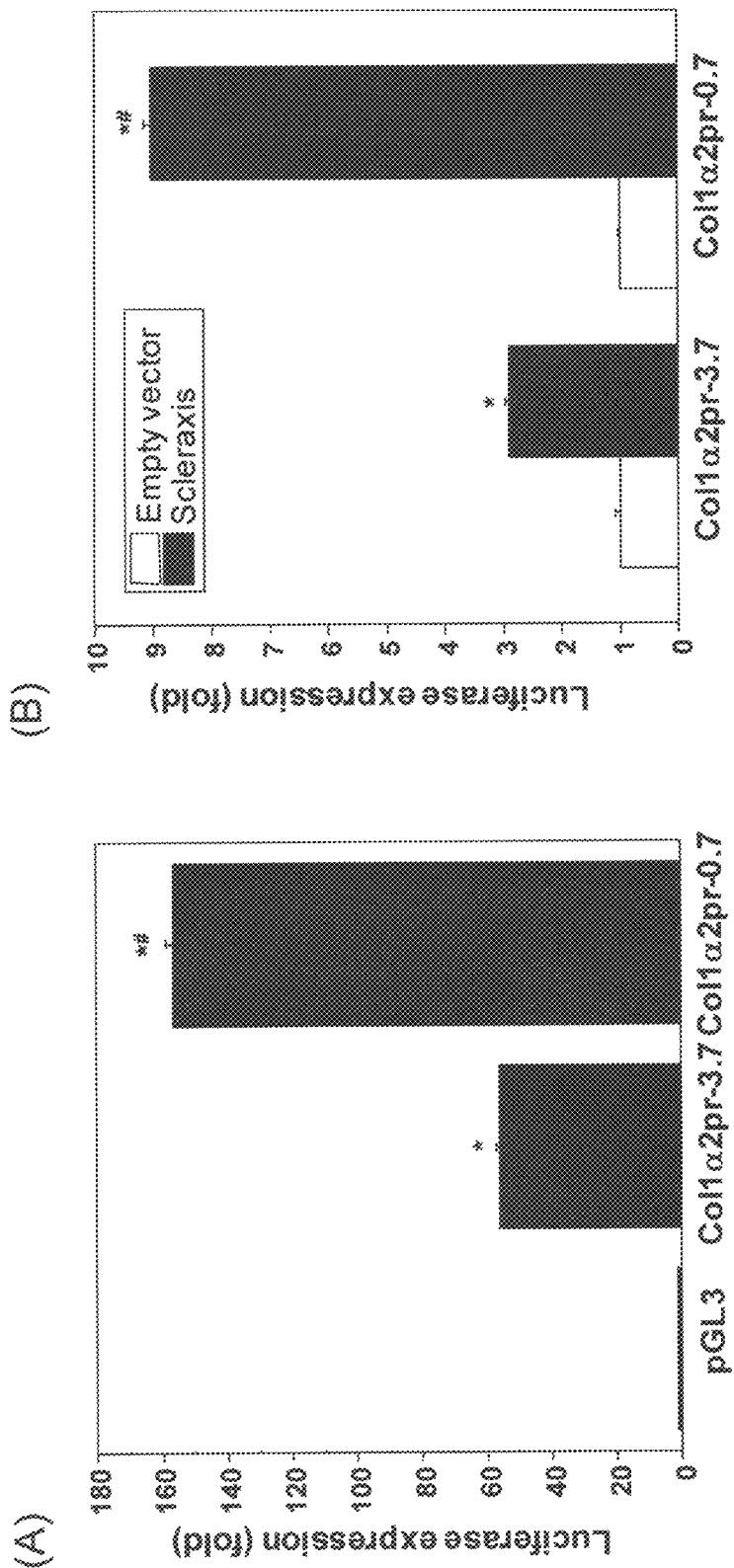
FIG. 8(A) is a chart showing scleraxis transactivation of the human COL1α2 proximal promoter in NIH 3T3 fibroblasts in comparison to an empty pGL3 vector.
FIG. 8(B) is a chart showing scleraxis transactivation of COL1α2 proximal promoter in NIH 3T3 fibroblasts in comparison to an empty pECE vector.

A study was done to compare the relative transactivation by scleraxis of the proximal COL1α2 gene promoter (COL 1α2pr-0.7) with the full-length 3.7 kb promoter (COL 1α2pr-3.7). NIH 3T3 fibroblasts were cultured in DMEM supplemented with 10% FBS, 1% penicillin/streptomycin, and 1% L-glutamine. The cells were seeded 24 h in 6-well culture plates in order to reach 70% confluence prior to transfection. Samples were co-transfected with 500 ng reporter plasmid (COL1α2 full-length 3.7 kb or 0.7 kb proximal promoters). Controls received an empty pGL3 Basic vector. Each of the test and control samples also received 500 ng scleraxis expression vector (pECE-HA-FLAG-Scx) and Renila luciferase expression vector (pRL) as a transfection control. The luciferase activity in each sample was assayed after 24-h incubation. The study was done in triplicate and the data were used to normalize the empty pGL3 vector data, and are reported as means±SD (FIG. 8(A)). The study was repeated using empty pECE vectors as controls (FIG. 8 (B)).

Example 4

Figure 9:
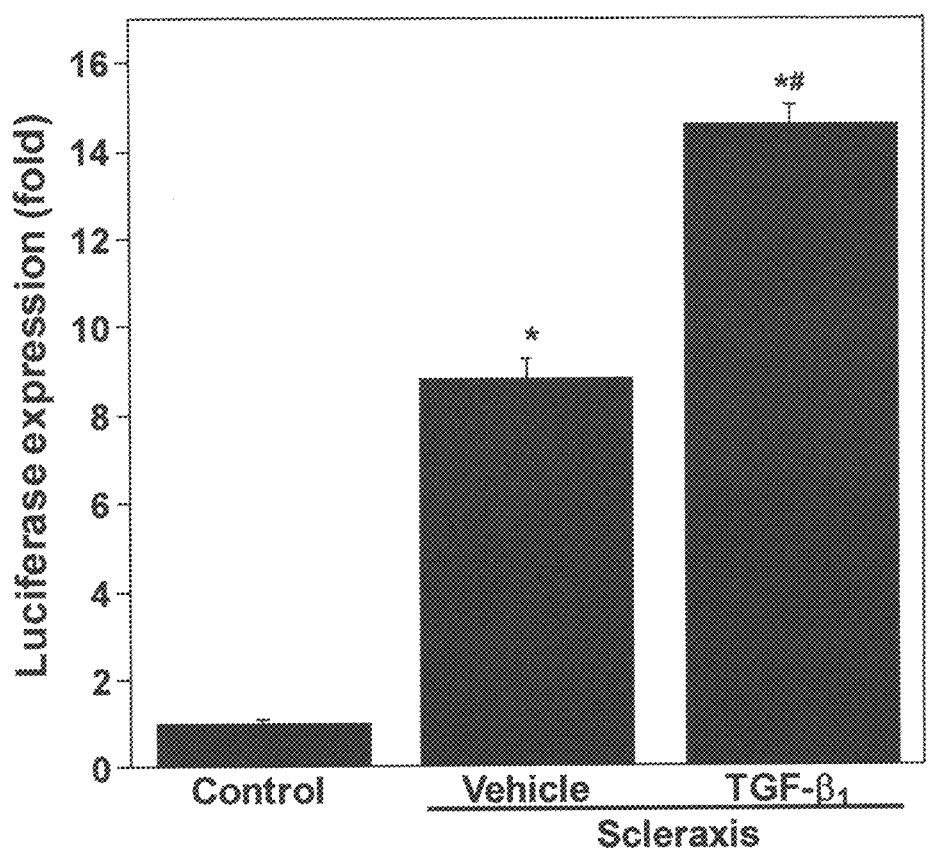
FIG. 9 is a chart showing augmentation by TGF-β of scleraxis-mediated transactivation of the human COL1α2 proximal promoter in NIH 3T3 fibroblasts in comparison to an empty pECE vector.

A study was done in triplicate to assess the effects of TGF-$β_1$ on scleraxis-mediated transactivation of the proximal COL1α2 gene promoter. NIH 3T3 fibroblasts were transfected with empty pECE vectors (control) or scleraxis expression vectors, with the proximal COL1α2 luciferase reporter vector. After a 24-h incubation, the samples were treated with one of the vehicle or 10 ng/mL TGF-$β_1$ and then incubated for a further 24 h after which, the luciferase assay was performed on all samples. The results are shown in FIG. 9.

Example 5

Figure 10:
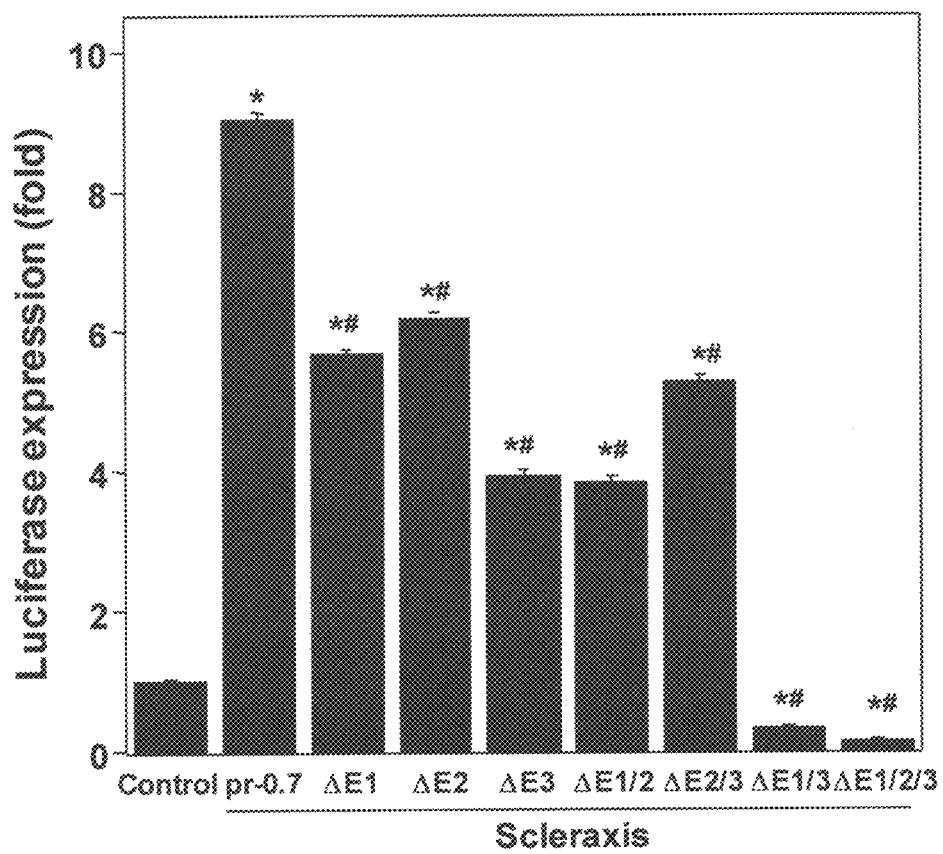
FIG. 10 is a chart showing the requirement of E boxes for scleraxis-mediated transactivation of the human COL1α2 proximal promoter in NIH 3T3 fibroblasts in comparison to an empty pECE vector.

To determine which, if any of the three putative E boxes i.e., E1, E2, E3, are involved in scleraxis-mediated transactivation of the COL1α2 gene promoter, mutation analysis studies were performed wherein single or multiple combinations of E boxes were mutated to prevent scleraxis binding in luciferase reporter studies. Point mutations were sequentially introduced to the three E boxes the proximal COL1α2 gene promoter individually or in combinations per the sequences shown in FIG. 3. Mutations were engineered to include novel restriction digest sites to facilitate screening of mutants. NIH 3T3 fibroblast cells were transfected with the COL1α2 0.7 kb proximal reporter (pr-0.7) plus empty pECE (control) or scleraxis expression vectors. Alternatively, 3T3 fibroblast cells were transfected with COL1α2 0.7 kb proximal reporters (pr-0.7) in which one or more E boxes had been mutated, plus the scleraxis expression vector. pRL was used as a transfection control. Luciferase assays were performed on the samples after they had been incubated for 24 h. The data shown in FIG. 10 are the means of three studies, normalized to the control empty vector.

Example 6

Mouse Scx nucleotide sequence SEQ ID NO:4 was tagged with FLAG and HA sequences and then incorporated into the pECE vector (SEQ ID NO:6). A scleraxis deletion mutant lacking the DNA binding basic domain (SEQ ID NO:7; FIG. 3(B)) was generated from the parent vector pECE-HA-FLAG-Scx (SEQ ID NO:6) by nested PCR. The nucleotide sequence of basic domain deletion ScxΔBD mutant after removal of the FLAG and HA tags is shown in SEQ ID NO:5 (FIG. 2(C)). FIG. 2(B) shows the location of the deleted nucleotides (i.e., indicated by "***").

Figure 11:
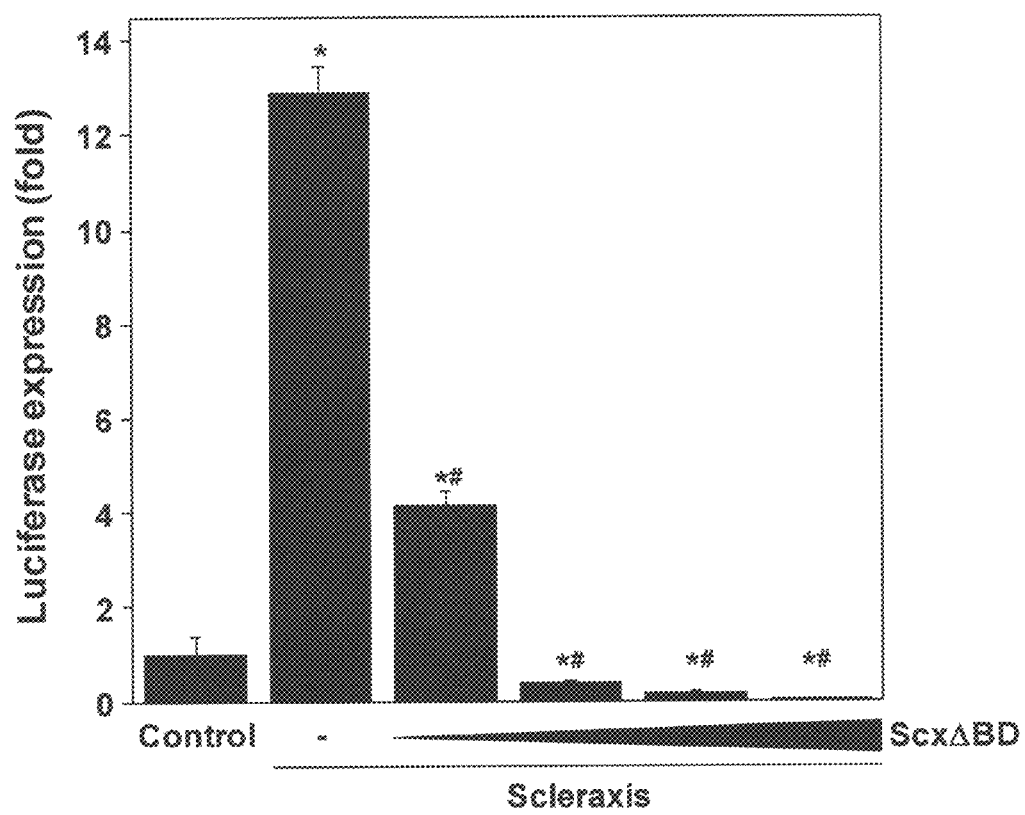
FIG. 11 is a chart showing that a scleraxis basic domain deletion mutant ScxΔBD abrogates scleraxis-mediated transactivation of the human COL1α2 proximal promoter in a dominant negative fashion.

The basic domain deletion ScxΔBD mutant was shown to be completely unable to transactivate the proximal COL1α2 gene promoter. Furthermore, the basic domain deletion ScxΔBD mutant also blocked the expression of the collagen Iα2 promoter luciferase reporter thereby indicating that the basic domain deletion ScxΔBD mutant functions as a dominant negative regulator of scleraxis-mediated gene expression. NIH 3T3 fibroblasts were transfected with the proximal COL1α2 gene promoter plus empty pECE (control) or with scleraxis expression vector SEQ ID NO:6 or with basic domain deletion ScxΔBD mutant SEQ ID NO:7. Some NIH 3T3 fibroblast cells were also transfected with 20 ng or 100 ng or 250 ng or 500 ng of the basic domain deletion ScxΔBD mutant SEQ ID NO:7. pRL was used as a transfection control. Luciferase assays were performed after the samples had been incubated for 24 h. The study was performed in triplicate, the data averaged and normalized to pECE, and are shown in FIG. 11. The data demonstrate that the basic domain deletion ScxΔBD mutant was unable to transactivate the proximal COL 1α2 gene promoter and acted as a dominant negative regulator of scleraxis-mediated gene expression.

Example 7

Figure 12:
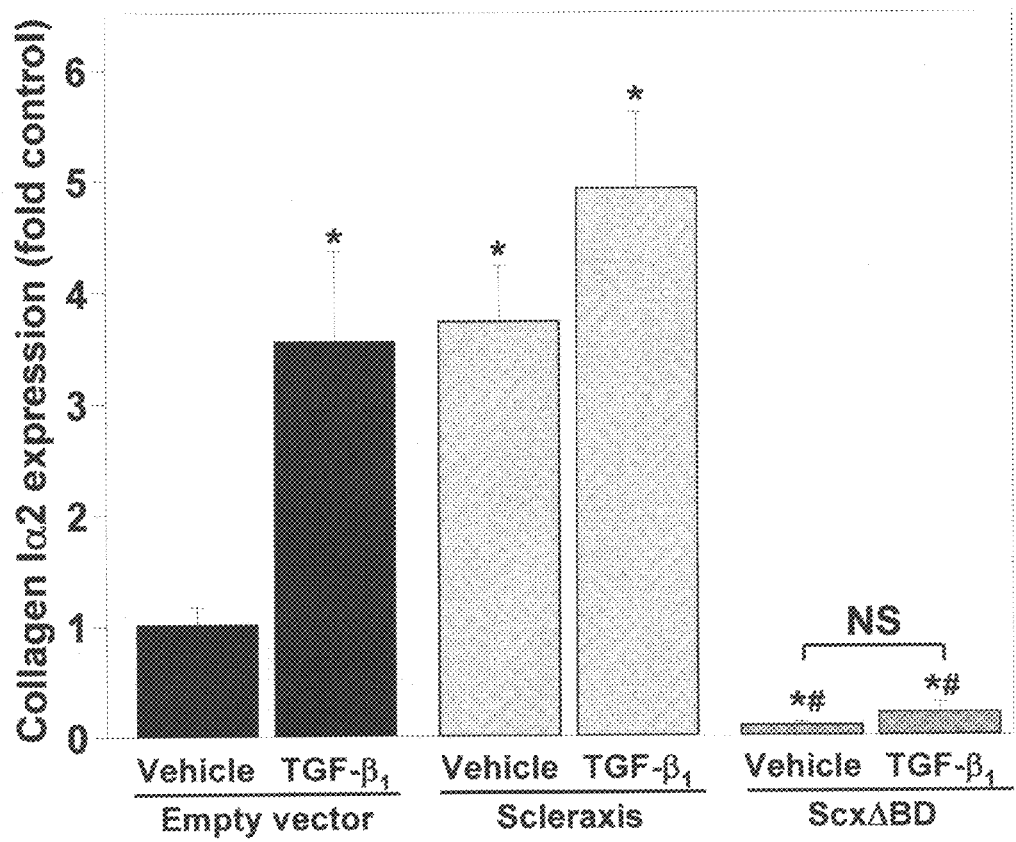
FIG. 12 is a chart showing that the scleraxis basic domain deletion mutant ScxΔBD blocks TGF-$β_1$-induced expression of COL1α2 gene expression.

A study was done to determine if the scleraxis dominant negative ScxΔBD mutant blocks TGF-$β_1$— induced COL1α2 gene expression. NIH 3T3 fibroblast cells were transfected with empty pECE vectors or with scleraxis expression vector SEQ ID NO:6 or with basic domain deletion ScxΔBD mutant SEQ ID NO:7. After a 24-h incubation, the cells were treated with the vehicle or with 10 ng/mL TGF-$β_1$. After a further 24-h incubation, the total RNA was isolated from each of the samples for analysis by quantitative RT-PCR. The abundance of COL1α2 mRNA was calculated using the $2^{-\Delta\Delta CT}$ method and was normalized to GAPDH. The study was done in triplicate. The results were normalized to the empty vector+vehicle samples and are shown in FIG. 12. The data confirm that the protein expressed by the basic domain deletion ScxΔBD mutant interferes with TGF-$β_1$-induced COL1α2 gene expression.

Example 8

Figure 13:
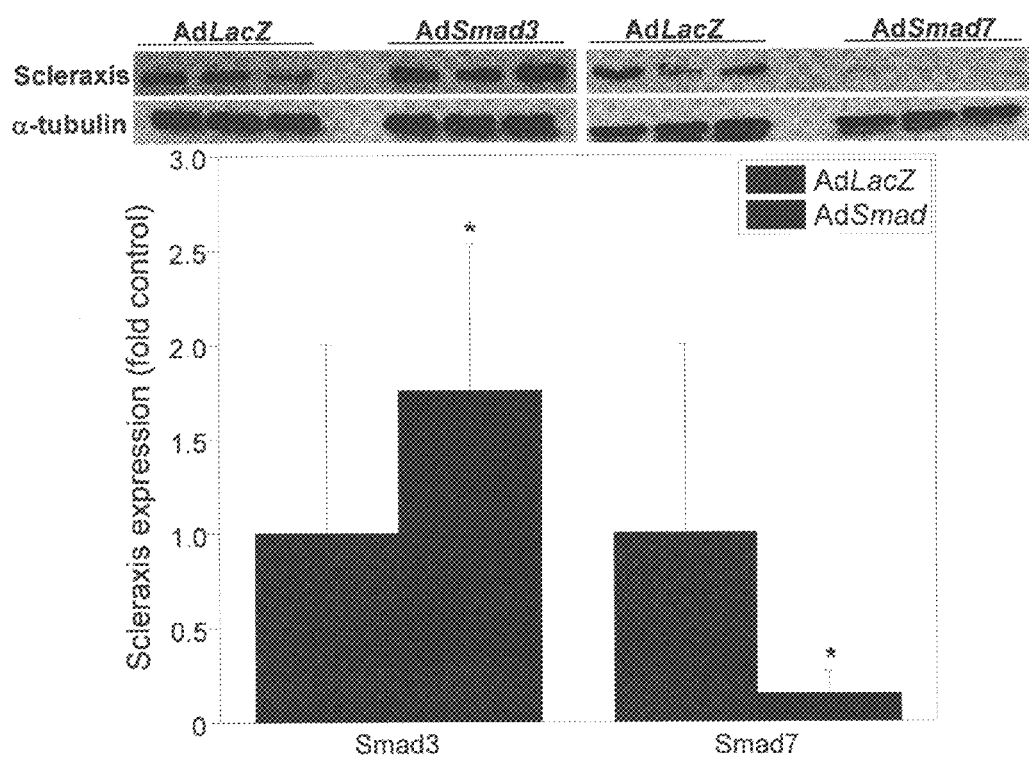
FIG. 13 is a chart showing that adenoviral delivery of Smad3 or Smad7 in isolated adult rat cardiac fibroblasts, augments or blunts the endogenous scleraxis protein expression respectively.

A study was done to examine the potential interaction of Scx and the canonical Smad signaling pathway. Isolated adult rat cardiac fibroblasts were infected with adenoviral constructs encoding pro-fibrotic Smad3 (MOI 10), anti-fibrotic Smad7 (MOI100) or LacZ as control (MOI 10 or 100). Twenty four hours after treatment, total cell protein was isolated for western blotting and α-tubulin was used as loading control. The data are shown in FIG. 13. The results represent three independent experiments, normalized to α-tubulin, and are reported as mean±standard error; *$P<0.05$ vs. Control (AdLacZ).

TGF-$β_1$ augmented transactivation of the COLIα2 proximal promoter by scleraxis. Conversely, our preliminary data showed that anti-fibrotic Smad7 blunted, but did not eliminate, Scx-mediated COLIα2 promoter transactivation. Together, these results suggest that Scx and Smads may co-regulate COLIα2 gene expression, possibly via parallel mechanisms. Smad3 up-regulated gene expression of Scx itself in primary rat cardiac fibroblasts, whereas Smad7 had the opposite effect, providing insight into our earlier observation that TGF-$β_1$ induced Scx expression. Smad3, the downstream pro-fibrotic effector of TGF-b1 signaling, increased scleraxis protein expression.

Example 9

Figure 14:
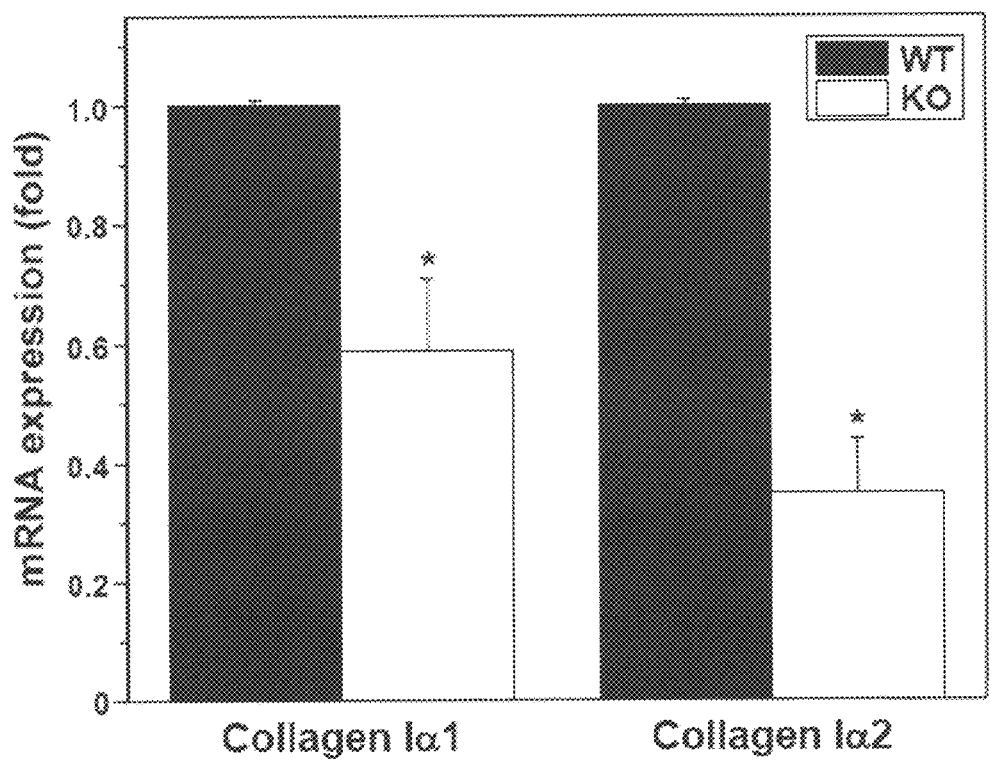
FIG. 14 is a chart showing that type I collagen components col Iα1 and col Iα2 are significantly down-regulated in scleraxis knock-out mice (KO) compared to wild type (WT) control mice.

A study was done to determine type I collagen (col Iα1 and col Iα2) expression in 3-5 wild type and scleraxis knock-out mice. Type I collagen is the main type expressed in the heart and is up-regulated in fibrosis. The data in FIG. 14 demonstrate that both components of type I collagen (col Iα1 and col Iα2) are significantly down-regulated in scleraxis knock-out mice, thereby confirming that blocking scleraxis function will be beneficial in fibrosis.

Example 10

Figure 15:
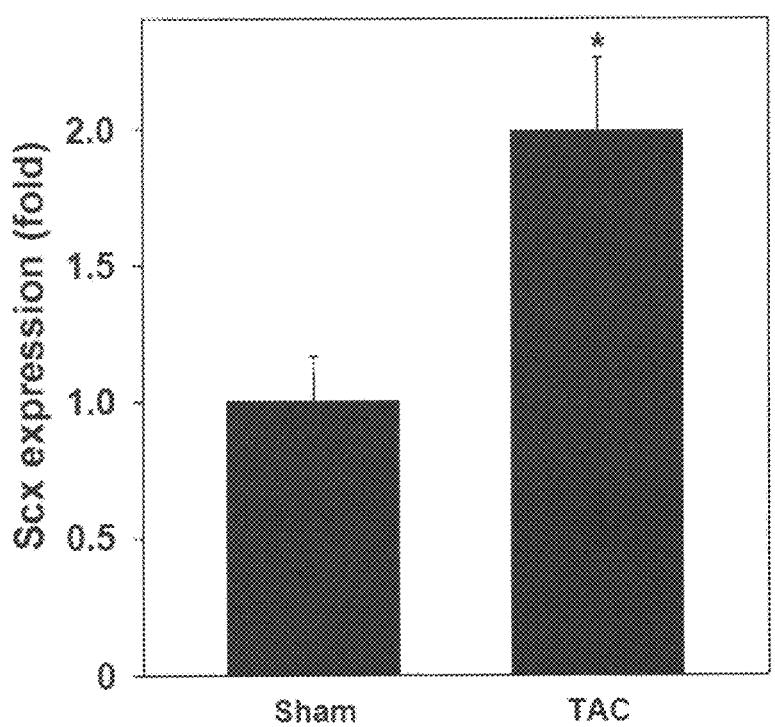
FIG. 15 is a chart showing that scleraxis expression is significantly increased by aortic banding of TAC mice bearing a GFP reporter. TAC refers to thoracic aortic constriction, done to induce fibrosis.

Mice bearing a GFP reporter under control of the scleraxis gene promoter (Scx-GFP mice) were subjected to aortic banding surgery, in which the transverse aorta was constricted with a suture to increase afterload. Sham controls underwent surgery, but the suture was not placed. Eight weeks later, hearts were collected and total RNA isolated. Scleraxis gene expression was assayed by quantitative real-time RT-PCR (qPCR) using scleraxis-specific primers. GAPDH was used as an internal control. The data are shown in FIG. 15. The results represent mean+/− standard error for 3 animals per group, and were normalized to sham control values. *$P<0.05$ versus sham control. The results demonstrate that scleraxis expression was significantly increased by aortic banding and confirm that scleraxis drives fibrosis in pathologic situations.

Example 11

The previous studies have shown that there are three potential site to which scleraxis might bind in the collagen Iα2 promoter (E1, E2 and E3) (see FIG. 6). Therefore, a study was done to determine if and where scleraxis actually binds to the collagen Iα2 gene promoter in primary cells. Isolated human cardiac fibroblasts were purchased from Cell Applications Inc. (Burlington, ON, CA) and were cultured on Fibroblast Growth Medium (FGM) (Cell Applications Inc.), initially in 15 mL FGM in T75 flasks followed by subculturing in fresh FGM at a density of 10,000 cells/cm.

Chromatin immunoprecipitation was performed on human cardiac fibroblasts using anti-scleraxis (Scx) antibody or non-specific IgG, following the method taught by Czubryt et al. (2003, *Regulation of peroxisome proliferator-activated receptor gamma coactivator 1alpha (PGC-1 alpha) and*

*mitochondrial function by MEF2 and HDAC5.* Proc Natl Acad Sci USA 100:1711-1716, 2003). PCR primers were used to amplify the collagen 1α2 promoter sequence flanking E-boxes 1 and 2 (E1/E2) or E-box 3 (E3)(see FIG. 6). Genomic DNA was used as an input positive control.

Figure 16:
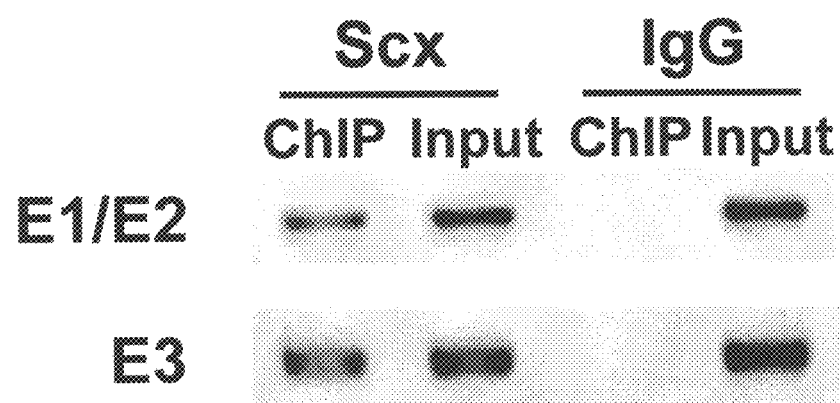
FIG. 16 is a micrograph showing binding of scleraxis to E-boxes 1 and 2 (E1/E2) and E-box 3 (E3) flanking the human COL1α2 proximal promoter.

The data in FIG. 16 show that scleraxis binds to both the E1/E2 and E3 sites. However, it should be noted that chromatin precipitation cannot be used to precisely discern whether scleraxis actually binds to E1 or E2 since they are only 12 nucleotides apart—well below the resolution of this technique. However, based on our earlier data where wherein each site was mutated individually (FIG. 10), it is most likely that scleraxis binds to E1. Second, it cannot be ruled out that the bands that occurred for E1/E2 and for E3 are not actually the same band, because E3 is close enough to E1/E2 that again the resolution issue may come into play. However, based on the earlier mutation study, it is arguable that it is likely that scleraxis binds to both E1 and E3.

Example 12

Figure 17:
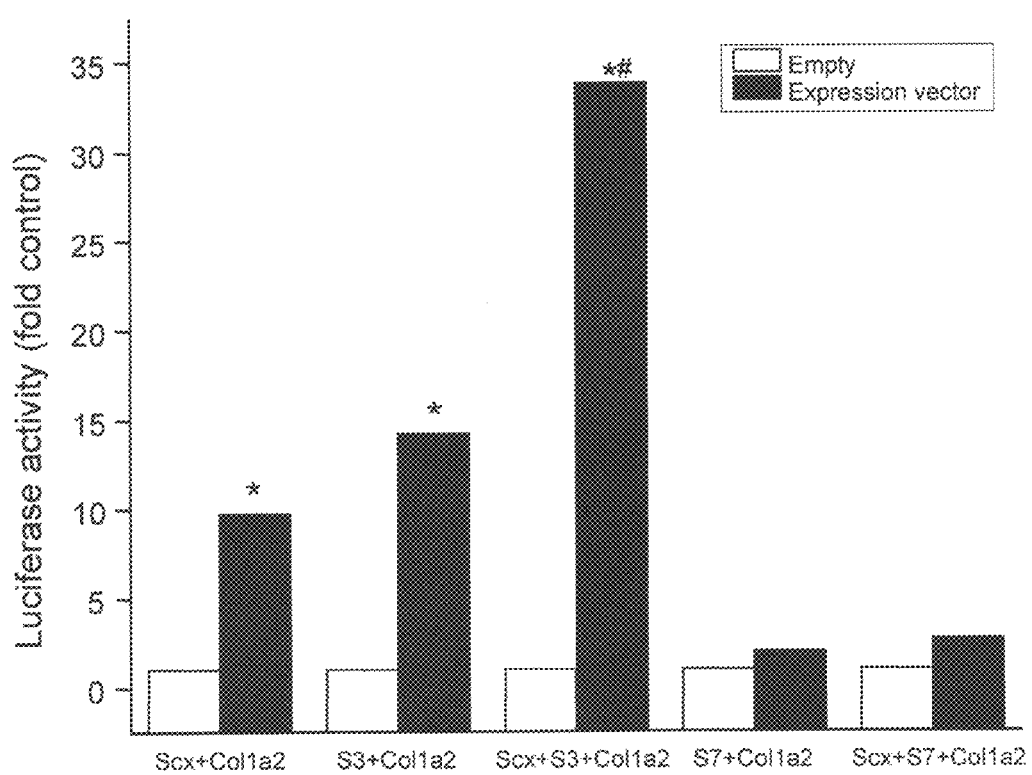
FIG. 17 is a chart showing the synergistic effects of scleraxis and Smad3 on the activation of the collagen 1α2 proximal promoter.

We performed luciferase assays using the human COL1α2 proximal gene promoter transfected into NIH 3T3 fibroblasts, along with either empty expression vector pECE, or intact scleraxis (Scx) or Smad3 (S3) or Smad7 (S7), alone or in combination. The data in FIG. 17 show that scleraxis proteins and receptor-regulated Smads work synergistically to regulate the collagen 1α2 proximal promoter (note that * indicates $p<0.05$ compared to the empty vector; # indicates $p<0.05$ compared to Scx or to S3). Increasing the levels of scleraxis alone caused about a 10% increase in activation of the collagen 1α2 proximal promoter, while increasing the levels of Smad3 alone resulted in about a 15% increase in activation of the collagen 1α2 proximal promoter. However, when the levels of both scleraxis and Smad3 were increased concurrently, there was a 35% increase in activation of the collagen 1α2 proximal promoter.

Example 13

Figure 18:
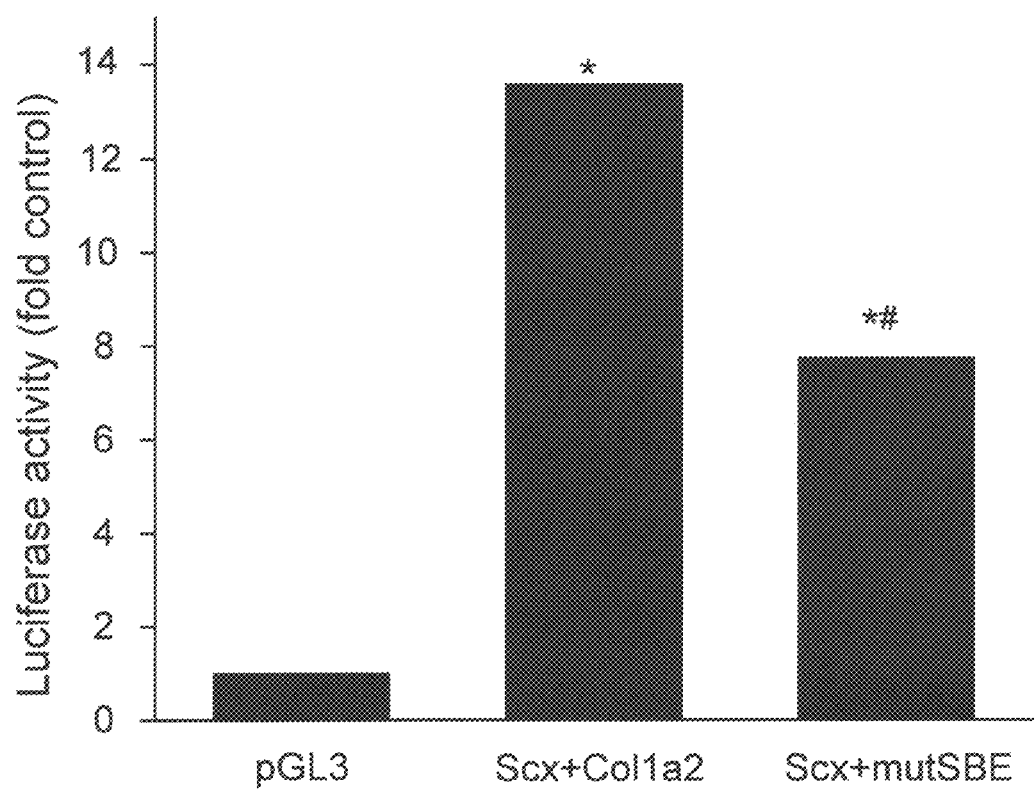
FIG. 18 is a chart showing the effects of mutating the Smad binding element on the collagen 1α2 proximal promoter on its induction by scleraxis.

We performed luciferase assays in NIH 3T3 fibroblasts transfected with a scleraxis (Scx) expression vector, plus an empty reporter (pGL3) or an intact proximal human COL1α2 gene promoter (Col1α2) or the proximal human COL1α2 gene promoter in which the Smad-binding element had been mutated to prevent Smad3 binding (mut SBE)." The data in FIG. 18 show that mutating the Smad binding element in the collagen 1α2 proximal promoter significantly reduced the ability of scleraxis to activate the collagen 1α2 proximal promoter (note that * indicates $p<0.05$ compared to the empty vector; # indicates $p<0.05$ compared to Scx+Col 1α2).

Example 14

Figure 19:
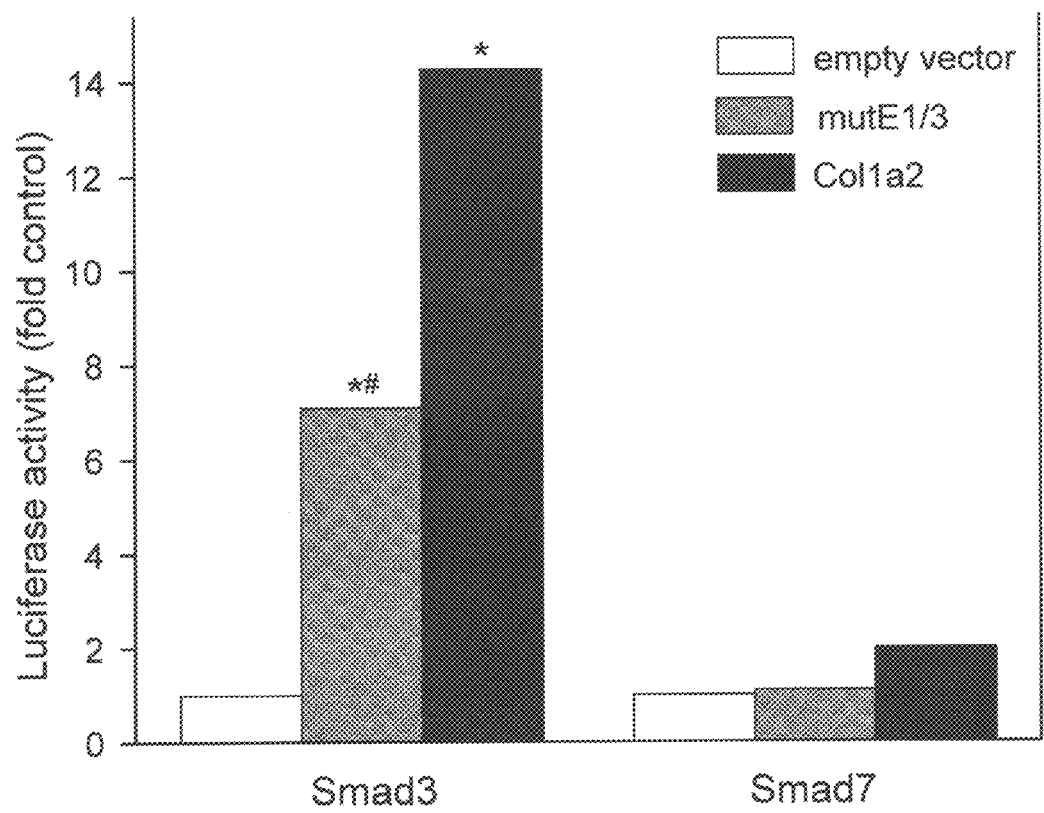
FIG. 19 is a chart showing the effects of mutating scleraxis binding sites E1 and E3 on Smad3 activation of the collagen 1α2 proximal promoter.

We performed luciferase assays in NIH 3T3 fibroblasts transfected with Smad3 or Smad7, plus an empty reporter vector or an intact proximal human COL gene promoter (Col 1α2) or the proximal human COL1α2 gene promoter in which the E1 and E3 scleraxis binding sites (mutE1/3) had been mutated to prevent scleraxis binding. The data in FIG. 19 show that mutating scleraxis binding sites E1 and E3 significantly reduced the ability of Smad3 to activate the collagen 1α2 proximal promoter (note that * indicates $p<0.05$ compared to the empty vector; # indicates $p<0.05$ compared to the intact Col 1α2 vector).

This disclosure demonstrates clearly that there is a synergistic interaction between scleraxis and receptor-regulated Smads to regulate activation of the collagen 1α2 promoter which is responsible for collagen production. Moreover, interfering with the binding ability of either scleraxis or receptor-regulated Smads significantly reduces, i.e., by about 50%, the activation of the collagen 1α2 proximal promoter. This discovery in combination with the discovery that the ScxΔBD DNA-binding mutant that completely attenuates Smad-mediated activation of the collagen 1α2 promoter, indicates that a physical interaction between scleraxis and a receptor-regulated Smad is required for full activation of the collagen 1α2 promoter. Accordingly, these discoveries make it possible to devise therapies for reducing, inhibiting, interfering with, stopping, preventing expression, production, accumulation of collagen production in mammalian cells and tissues. Such therapies may draw on the options of: (i) selectively interfering with the ability of scleraxis to bind to DNA thereby partially reducing but not eliminating the activation of the collagen 1α2 promoter, (ii) selectively interfering with the ability of a receptor-regulated Smad to bind to DNA thereby partially reducing but not eliminating the activation of the collagen 1α2 promoter, (iii) selective use of the ScxΔBD DNA-binding mutant that binds to receptor-regulated Smads thereby preventing their binding to DNA. The therapies may be provided by administration of selected compositions, alone or in combination to bind to target binding sites and/or target molecules, i.e., scleraxis, receptor-regulated Smads.

The above-described embodiments have been provided as examples, for clarity in understanding the invention. A person of skill in the art will recognize that alterations, modifications and variations may be effected to the embodiments described above while remaining within the scope of the invention as defined by the claims appended hereto.

The invention claimed is:

1. A method for reducing collagen production in mammalian cells, comprising administering to a subject in need thereof, a composition comprising an effective amount of a nucleotide sequence set forth in SEQ ID NO:5 for in vivo expression of the amino acid sequence set forth in SEQ ID NO:8 in an amount sufficient to interfere with in vivo activation and/or expression of a collagen 1α2 proximal promoter.

2. The method according to claim 1, wherein the method comprises interfering with a synergistic interaction between a scleraxis protein and a receptor-regulated Smad.

3. The method according to claim 2, wherein the method comprises interfering with an in vivo production of a scleraxis protein.

4. The method according to claim 2, wherein the method comprises interfering with binding of a scleraxis protein with a scleraxis protein-binding site.

5. The method according to claim 2, wherein the method comprises interfering with an in vivo production of a receptor-regulated Smad.

6. The method according to claim 2, wherein the method comprises interfering with binding of a receptor-regulated Smad with a Smad-binding site.

* * * * *

SEQUENCE LISTING

<160> NUMBER OF SEQ ID NOS: 14

<210> SEQ ID NO 1
<211> LENGTH: 207
<212> TYPE: PRT
<213> ORGANISM: Mus musculus

<400> SEQUENCE: 1

Met Ser Phe Ala Met Leu Arg Ser Ala Pro Pro Gly Arg Tyr Leu
1               5                   10                  15

Tyr Pro Glu Val Ser Pro Leu Ser Glu Asp Glu Asp Arg Gly Ser Glu
            20                  25                  30

Ser Ser Gly Ser Asp Glu Lys Pro Cys Arg Val His Ala Ala Arg Cys
        35                  40                  45

Gly Leu Gln Gly Ala Arg Arg Arg Ala Gly Gly Arg Arg Ala Ala Gly
    50                  55                  60

Ser Gly Pro Gly Pro Gly Arg Pro Gly Glu Pro Arg Gln Arg
65              70                  75                  80

His Thr Ala Asn Ala Arg Glu Arg Asp Arg Thr Asn Ser Val Asn Thr
                85                  90                  95

Ala Phe Thr Ala Leu Arg Thr Leu Ile Pro Thr Glu Pro Ala Asp Arg
            100                 105                 110

Lys Leu Ser Lys Ile Glu Thr Leu Arg Leu Ala Ser Ser Tyr Ile Ser
            115                 120                 125

His Leu Gly Asn Val Leu Leu Val Gly Glu Ala Cys Gly Asp Gly Gln
        130                 135                 140

Pro Cys His Ser Gly Pro Ala Phe Phe His Ser Gly Arg Ala Gly Ser
145                 150                 155                 160

Pro Leu Pro Pro Pro Pro Pro Pro Leu Ala Arg Asp Gly Gly
                165                 170                 175

Glu Asn Thr Gln Pro Lys Gln Ile Cys Thr Phe Cys Leu Ser Asn Gln
                180                 185                 190

Arg Lys Leu Ser Lys Asp Arg Asp Arg Lys Thr Ala Ile Arg Ser
        195                 200                 205

<210> SEQ ID NO 2
<211> LENGTH: 209
<212> TYPE: PRT
<213> ORGANISM: Rattus norvegicus

<400> SEQUENCE: 2

Met Ser Phe Ala Met Leu Arg Ser Ala Pro Pro Gly Arg Tyr Leu
1               5                   10                  15

Tyr Pro Glu Val Ser Pro Leu Ser Glu Asp Glu Asp Arg Gly Ser Glu
            20                  25                  30

Ser Ser Gly Ser Asp Glu Lys Pro Cys Arg Val His Ala Ala Arg Cys
        35                  40                  45

Gly Leu Gln Gly Ala Arg Arg Arg Ala Gly Gly Arg Arg Ala Ala Gly
    50                  55                  60

Ser Gly Pro Gly Pro Gly Arg Pro Gly Glu Pro Arg Gln Arg
65              70                  75                  80

His Thr Ala Asn Ala Arg Glu Arg Asp Arg Thr Asn Ser Val Asn Thr
                85                  90                  95

Ala Phe Thr Ala Leu Arg Thr Leu Ile Pro Thr Glu Pro Ala Asp Arg
            100                 105                 110

Lys Leu Ser Lys Ile Glu Thr Leu Arg Leu Ala Ser Ser Tyr Ile Ser
            115                 120                 125

His Leu Gly Asn Val Leu Leu Val Gly Glu Ala Cys Gly Asp Gly Gln
        130                 135                 140

Pro Cys His Ser Gly Pro Ala Phe Phe His Ser Gly Arg Ala Gly Ser
145                 150                 155                 160

```
Pro Leu Pro Pro Pro Pro Pro Pro Leu Pro Ala Arg Asp
            165                 170                 175

Gly Gly Glu Asn Thr Gln Pro Lys Gln Ile Cys Thr Phe Cys Leu Ser
            180                 185                 190

Asn Gln Arg Lys Leu Ser Lys Asp Arg Asp Arg Lys Thr Ala Ile Arg
            195                 200                 205

Ser

<210> SEQ ID NO 3
<211> LENGTH: 201
<212> TYPE: PRT
<213> ORGANISM: Homo sapiens

<400> SEQUENCE: 3

Met Ser Phe Ala Thr Leu Arg Pro Ala Pro Pro Gly Arg Tyr Leu Tyr
1               5                   10                  15

Pro Glu Val Ser Pro Leu Ser Glu Asp Glu Arg Gly Ser Asp Ser
            20                  25                  30

Ser Gly Ser Asp Glu Lys Pro Cys Arg Val His Ala Ala Arg Cys Gly
            35                  40                  45

Leu Gln Gly Ala Arg Arg Ala Gly Gly Arg Ala Gly Gly Gly
        50                  55                  60

Gly Pro Gly Gly Arg Pro Gly Arg Glu Pro Arg Gln Arg His Thr Ala
65                  70                  75                  80

Asn Ala Arg Glu Arg Asp Arg Thr Asn Ser Val Asn Thr Ala Phe Thr
                85                  90                  95

Ala Leu Arg Thr Leu Ile Pro Thr Glu Pro Ala Asp Arg Lys Leu Ser
                100                 105                 110

Lys Ile Glu Thr Leu Arg Leu Ala Ser Ser Tyr Ile Ser His Leu Gly
                115                 120                 125

Asn Val Leu Leu Ala Gly Glu Ala Cys Gly Asp Gly Gln Pro Cys His
        130                 135                 140

Ser Gly Pro Ala Phe Phe His His Ala Ala Arg Ala Gly Ser Pro Pro
145                 150                 155                 160

Pro Pro Pro Pro Pro Ala Arg Asp Gly Glu Asn Thr Gln Pro Lys
                165                 170                 175

Gln Ile Cys Thr Phe Cys Leu Ser Asn Gln Arg Lys Leu Ser Lys Asp
                180                 185                 190

Arg Asp Arg Lys Thr Ala Ile Arg Ser
        195                 200

<210> SEQ ID NO 4
<211> LENGTH: 624
<212> TYPE: DNA
<213> ORGANISM: Homo sapiens

<400> SEQUENCE: 4
atgtccttcg ccatgctgcg ttcagcgccg ccgccgggtc gctacctgta ccctgaggtg      60
agcccgctgt cggaggatga ggaccgcgga agcgagagct cgggctccga cgagaaaccc     120
tgccgtgtgc atgctgcgcg ctgtggcctc cagggcgccc ggcggcgggc aggaggacgg     180
agggccgcgg gtagcgggcc aggacccggg gggcggccag gccgcgagcc ccggcagcgc     240
cacacagcga atgcgcgcga gcgggaccgc accaacagcg tgaacacggc cttcactgcg     300
```

```
ctgcgcacac tcatccccac cgagccagcg gaccgcaagc tctccaagat tgagacgctg      360
cgcctggcct ccagctacat ttctcacctg ggcaatgtgc tgctggtggg tgaggcctgt      420
ggcgacgggc aaccatacat ttctcacctg ggcaatgtgc tgctggtggg tgaggcctgt      480
ggcgacgggc aaccatcgcc gccaccacca ctggccagag acggcggcga gaacacccag      540
cccaaacaga tctgcacgcc gccaccacca ctggccagag acggcggcga gaacacccag      600
cccaaacaga tctgcagaag ttag                                              624
```

<210> SEQ ID NO 5
<211> LENGTH: 585
<212> TYPE: DNA
<213> ORGANISM: Artificial Sequence
<220> FEATURE:
<223> OTHER INFORMATION: Scleraxis nucleotide sequence with a deleted
      binding domain (the scleraxis basic domain deletion mutant)

<400> SEQUENCE: 5

```
atgtccttcg ccatgctgcg ttcagcgccg ccgccgggtc gctacctgta ccctgaggtg       60
agcccgctgt cggaggatga ggaccgcgga agcgagagct cgggctccga cgagaaaccc      120
tgccgtgtgc atgctgcgcg ctgtggcctc cagggcgccc ggcggcgggc aggaggacgg      180
agggccgcgg gtagcgggcc aggacccggg gggcggccag gccgcgagcc caccaacagc      240
gtgaacacgg ccttcactgc gctgcgcaca ctcatcccca ccgagccagc ggaccgcaag      300
ctctccaaga ttgagacgct gcgcctggcc tccagctaca tttctcacct gggcaatgtg      360
ctgctggtgg gtgaggcctg tggcgacggg caaccataca tttctcacct gggcaatgtg      420
ctgctggtgg gtgaggcctg tggcgacggg caaccatcgc cgccaccacc actggccaga      480
gacggcggcg agaacaccca gcccaaacag atctgcacgc cgccaccacc actggccaga      540
gacggcggcg agaacaccca gcccaaacag atctgcagaa gttag                     585
```

<210> SEQ ID NO 6
<211> LENGTH: 705
<212> TYPE: DNA
<213> ORGANISM: Artificial Sequence
<220> FEATURE:
<223> OTHER INFORMATION: Mouse scleraxis wild type nucleotide sequence
      with inserted FLAG and HA sequences

<400> SEQUENCE: 6

```
atggattaca aggacgacga cgataagatc tgtcgacggt accccgggga attctatccg       60
tatgatgtgc cggattatgc cgatgtcctt cgccatgctg cgttcagcgc cgccgccggg      120
tcgctacctg taccctgagg tgagcccgct gtcggaggat gaggaccgcg gaagcgagag      180
ctcgggctcc gacgagaaac cctgccgtgt gcatgctgcg cgctgtggcc tccagggcgc      240
cggcggcggg caggaggacg gagggccgcg ggtagcgggc caggacccgg gggcggcca      300 ggccgcgagc cccggcagcg gcacacagcg aatgcgcgcg agcgggaccg caccaacagc      360
gtgaacacgg ccttcactgc gctgcgcaca ctcatcccca ccgagccagc ggaccgcaag      420
ctctccaaga ttgagacgct gcgcctggcc tccagctaca tttctcacct gggcaatgtg      480
ctgctggtgg gtgaggcctg tggcgacggg caaccataca tttctcacct gggcaatgtg      540
ctgctggtgg gtgaggcctg tggcgacggg caaccatcgc cgccaccacc actggccaga      600
gacggcggcg agaacaccca gcccaaacag atctgcacgc cgccaccacc actggccaga      660
gacggcggcg agaacaccca gcccaaacag atctgcagaa gttag                     705
```

<210> SEQ ID NO 7
<211> LENGTH: 666
<212> TYPE: DNA
<213> ORGANISM: Artificial Sequence
<220> FEATURE:
<223> OTHER INFORMATION: Mouse scleraxis basic domain deletion mutant with inserted FLAG and HA sequences

<400> SEQUENCE: 7

```
atggattaca aggacgacga cgataagatc tgtcgacggt accccgggga attctatccg      60
tatgatgtgc cggattatgc gatgtccttc gccatgctgc gttcagcgcc gccgccgggt     120
cgctacctgt accctgaggt gagcccgctg tcggaggatg aggaccgcgg aagcgagagc     180
tcgggctccg acgagaaacc ctgccgtgtg catgctgcgc gctgtggcct ccagggcgcc     240
cggcggcggg caggaggacg gagggccgcg ggtagcgggc caggacccgg ggggcggcca     300
ggccgcgagc ccaccaacag cgtgaacacg gccttcactg cgctgcgcac actcatcccc     360
accgagccag cggaccgcaa gctctccaag attgagacgc tgcgcctggc ctccagctac     420
atttctcacc tgggcaatgt gctgctggtg ggtgaggcct gtggcgacgg caaccatac      480 atttctcacc tgggcaatgt gctgctggtg ggtgaggcct gtggcgacgg caaccatcg      540 ccgccaccac cactggccag agacggcggc gagaacaccc agcccaaaca gatctgcacg     600
ccgccaccac cactggccag agacggcggc gagaacaccc agcccaaaca gatctgcaga     660
agttag                                                                666
```

<210> SEQ ID NO 8
<211> LENGTH: 194
<212> TYPE: PRT
<213> ORGANISM: Artificial Sequence
<220> FEATURE:
<223> OTHER INFORMATION: Protein expressed by the mouse scleraxis basic domain deletion mutant with inserted FLAG and HA sequences

<400> SEQUENCE: 8

```
Met Ser Phe Ala Met Leu Arg Ser Ala Pro Pro Gly Arg Tyr Leu
1               5                   10                  15

Tyr Pro Glu Val Ser Pro Leu Ser Glu Asp Glu Asp Arg Gly Ser Glu
                20                  25                  30

Ser Ser Gly Ser Asp Glu Lys Pro Cys Arg Val His Ala Ala Arg Cys
            35                  40                  45

Gly Leu Gln Gly Ala Arg Arg Arg Ala Gly Arg Ala Ala Gly
        50                  55                  60

Ser Gly Pro Gly Pro Gly Gly Arg Pro Gly Arg Glu Pro Thr Asn Ser
65                  70                  75                  80

Val Asn Thr Ala Phe Thr Ala Leu Arg Thr Leu Ile Pro Thr Glu Pro
                85                  90                  95

Ala Asp Arg Lys Leu Ser Lys Ile Glu Thr Leu Arg Leu Ala Ser Ser
                100                 105                 110

Tyr Ile Ser His Leu Gly Asn Val Leu Leu Val Gly Glu Ala Cys Gly
            115                 120                 125
```

```
Asp Gly Gln Pro Cys His Ser Gly Pro Ala Phe Phe His Ser Gly Arg
        130                 135                 140

Ala Gly Ser Pro Leu Pro Pro Pro Pro Pro Pro Leu Ala Arg
145                 150                 155                 160

Asp Gly Gly Glu Asn Thr Gln Pro Lys Gln Ile Cys Thr Phe Cys Leu
                165                 170                 175

Ser Asn Gln Arg Lys Leu Ser Lys Asp Arg Asp Arg Lys Thr Ala Ile
            180                 185                 190

Arg Ser

<210> SEQ ID NO 9
<211> LENGTH: 6
<212> TYPE: DNA
<213> ORGANISM: Artificial Sequence
<220> FEATURE:
<223> OTHER INFORMATION: Putative E1 box binding site

<400> SEQUENCE: 9 caagtg                                                                    6

<210> SEQ ID NO 10
<211> LENGTH: 6
<212> TYPE: DNA
<213> ORGANISM: Artificial Sequence
<220> FEATURE:
<223> OTHER INFORMATION: Putative E2 box binding site

<400> SEQUENCE: 10 caggtg                                                                    6

<210> SEQ ID NO 11
<211> LENGTH: 6
<212> TYPE: DNA
<213> ORGANISM: Artificial Sequence
<220> FEATURE:
<223> OTHER INFORMATION: Putative E3 box binding site

<400> SEQUENCE: 11 cagctg                                                                    6

<210> SEQ ID NO 12
<211> LENGTH: 6
<212> TYPE: DNA
<213> ORGANISM: Artificial Sequence
<220> FEATURE:
<223> OTHER INFORMATION: Mutated E1 box

<400> SEQUENCE: 12 ccatgc                                                                    6

<210> SEQ ID NO 13
<211> LENGTH: 6
<212> TYPE: DNA
<213> ORGANISM: Artificial Sequence
<220> FEATURE:
<223> OTHER INFORMATION: Mutated E2 box

<400> SEQUENCE: 13 ctgcag                                                                    6

<210> SEQ ID NO 14
<211> LENGTH: 6
<212> TYPE: DNA
```

```
<213> ORGANISM: Artificial Sequence
<220> FEATURE:
<223> OTHER INFORMATION: Mutated E3 box

<400> SEQUENCE: 14 cccggg                                                                    6
```